United States Patent
Loshakove et al.

(10) Patent No.: US 7,060,084 B1
(45) Date of Patent: Jun. 13, 2006

(54) VASCULAR CLOSURE DEVICE

(75) Inventors: Amir Loshakove, Moshav-Bazra (IL); Ido Kilemnik, Herzolia (IL); Dvir Keren, Petach-Tikva (IL)

(73) Assignee: By-Pass, Inc., Orangeburg, NY (US)

( * ) Notice: Subject to any disclaimer, the term of this patent is extended or adjusted under 35 U.S.C. 154(b) by 0 days.

(21) Appl. No.: 09/936,789

(22) PCT Filed: Dec. 9, 1999

(86) PCT No.: PCT/IL99/00674

§ 371 (c)(1),
(2), (4) Date: Sep. 17, 2001

(87) PCT Pub. No.: WO00/56223

PCT Pub. Date: Sep. 28, 2000

Related U.S. Application Data

(63) Continuation-in-part of application No. 09/701,523, filed as application No. PCT/IL99/000285 on May 30, 1999, and a continuation-in-part of application No. 09/701,531, filed as application No. PCT/IL99/00284 on May 30, 1999, and a continuation-in-part of application No. 09/936,806, filed as application No. PCT/IL99/00670 on Sep. 17, 2001.

(30) Foreign Application Priority Data

May 29, 1998 (IL) ...................................... 124694
Mar. 19, 1999 (IL) ...................................... 129067

(51) Int. Cl.
*A61B 17/04* (2006.01)

(52) U.S. Cl. .................................................... 606/213

(58) Field of Classification Search ................ 606/216, 606/213
See application file for complete search history.

(56) References Cited

U.S. PATENT DOCUMENTS

| | | | |
|---|---|---|---|
| 3,586,002 A | | 6/1971 | Wood |
| 3,825,010 A | * | 7/1974 | McDonald |
| 4,069,826 A | | 1/1978 | Sessions et al. |
| 4,366,819 A | | 1/1983 | Kaster |
| 4,368,736 A | | 1/1983 | Kaster .......................... 606/153 |
| 4,387,879 A | | 6/1983 | Tauschinski |
| 4,485,816 A | | 12/1984 | Krumme |

(Continued)

FOREIGN PATENT DOCUMENTS

DE      28 22 603        11/1979

(Continued)

OTHER PUBLICATIONS

U.S. Appl. No. 09/187,361, published on May 18, 2000, Galdonik,J. A. et al., "Medical Graft Componentand Methods of Installing Same".

(Continued)

*Primary Examiner*—Gary Jackson
(74) *Attorney, Agent, or Firm*—Fenster and Company

(57) ABSTRACT

This invention is a device (500) for sealing a hole in a blood vessel, comprising a ring (504); a plurality of spikes (506) extending from said ring towards a center of said ring, and to first direction along an axis of said ring, said spikes being adapted for engaging a blood vessel; a plurality of tabs (502) extending substantially radially from said ring, wherein rotating said tabs around said ring distorts said ring such that said spikes are rotated in a same direction as said tabs.

30 Claims, 24 Drawing Sheets

U.S. PATENT DOCUMENTS

| | | | |
|---|---|---|---|
| 4,676,245 A * | 6/1987 | Fukuda | |
| 4,917,087 A | 4/1990 | Walsh et al. | |
| 4,930,502 A * | 6/1990 | Chen | |
| 4,930,674 A | 6/1990 | Barak | 227/179 |
| 4,997,439 A * | 3/1991 | Chen | |
| 5,047,047 A * | 9/1991 | Yoon | |
| 5,158,566 A * | 10/1992 | Pianetti | |
| 5,188,636 A | 2/1993 | Fedotov | |
| 5,222,974 A | 6/1993 | Kensey et al. | |
| 5,234,447 A | 8/1993 | Kaster et al. | |
| 5,254,127 A | 10/1993 | Wholey et al. | |
| 5,282,827 A | 2/1994 | Kensey et al. | |
| 5,478,353 A | 12/1995 | Yoon | |
| 5,478,354 A | 12/1995 | Tovey et al. | |
| 5,486,187 A | 1/1996 | Schenck | |
| 5,618,311 A | 4/1997 | Gryskiewicz | |
| 5,676,689 A | 10/1997 | Kensey et al. | |
| 5,707,393 A | 1/1998 | Kensey et al. | |
| 5,746,755 A | 5/1998 | Wood et al. | |
| 5,759,194 A | 6/1998 | Hammerslag | |
| 5,779,719 A | 7/1998 | Klein et al. | |
| 5,792,173 A | 8/1998 | Breen et al. | |
| 5,797,933 A | 8/1998 | Snow et al. | |
| 5,814,005 A | 9/1998 | Barra et al. | |
| 5,817,113 A | 10/1998 | Gifford, III et al. | |
| 5,861,004 A | 1/1999 | Kensey et al. | |
| 5,868,763 A * | 2/1999 | Spence et al. | 606/153 |
| 5,910,155 A | 6/1999 | Ratcliff et al. | |
| 5,922,000 A | 7/1999 | Chodorow | 606/167 |
| 5,935,147 A | 8/1999 | Kensey et al. | |
| 5,941,890 A | 8/1999 | Voegele et al. | |
| 5,948,425 A | 9/1999 | Janzen et al. | |
| 5,964,782 A | 10/1999 | Lafontaine et al. | |
| 5,976,159 A | 11/1999 | Bolduc et al. | |
| 5,993,476 A | 11/1999 | Groiso | |
| 6,004,341 A | 12/1999 | Zhu et al. | |
| 6,071,292 A | 6/2000 | Makower et al. | |
| 6,383,208 B1 | 5/2002 | Sancoff et al. | |

FOREIGN PATENT DOCUMENTS

| | | |
|---|---|---|
| DE | 31 47 609 | 6/1983 |
| EP | 0 744 237 | 5/1997 |
| WO | WO 97/07741 | 3/1997 |
| WO | WO 98/16161 | 4/1998 |
| WO | WO 98/32412 | 7/1998 |
| WO | WO 98/42262 | 10/1998 |
| WO | WO 00/27310 | 5/2000 |
| WO | WO 01/19256 | 3/2001 |

OTHER PUBLICATIONS

U.S. Appl. No. 09/187,364,published on May 18, 2000, Berg, T. A. et al., "Minimally Invasive RevascularizationApparatusand Methods".

U.S. Appl. No. 09/324,997,published on Sep. 14, 2000, Grudem,J. et al., "Medical Grafting Methods and Apparatus".

U.S. Appl. No. 60/137,764,published on Dec. 14, 2000, Logan,J. et al., "MechanicalAnastomosis Delivery Apparatus".

* cited by examiner

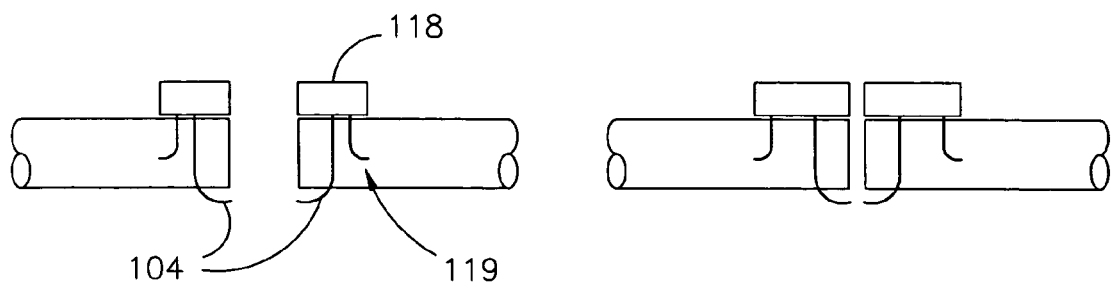
FIG.1H
FIG.1I
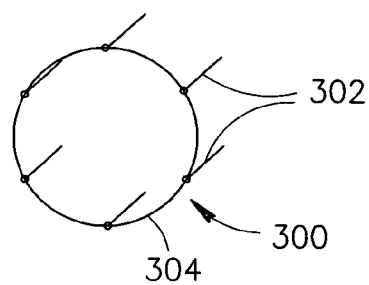
FIG.1J
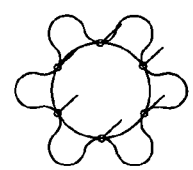
FIG.1K
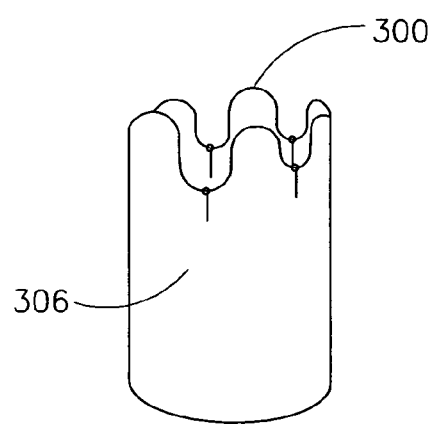
FIG.1L
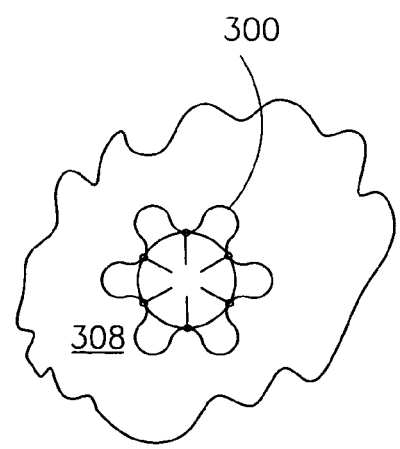
FIG.1M

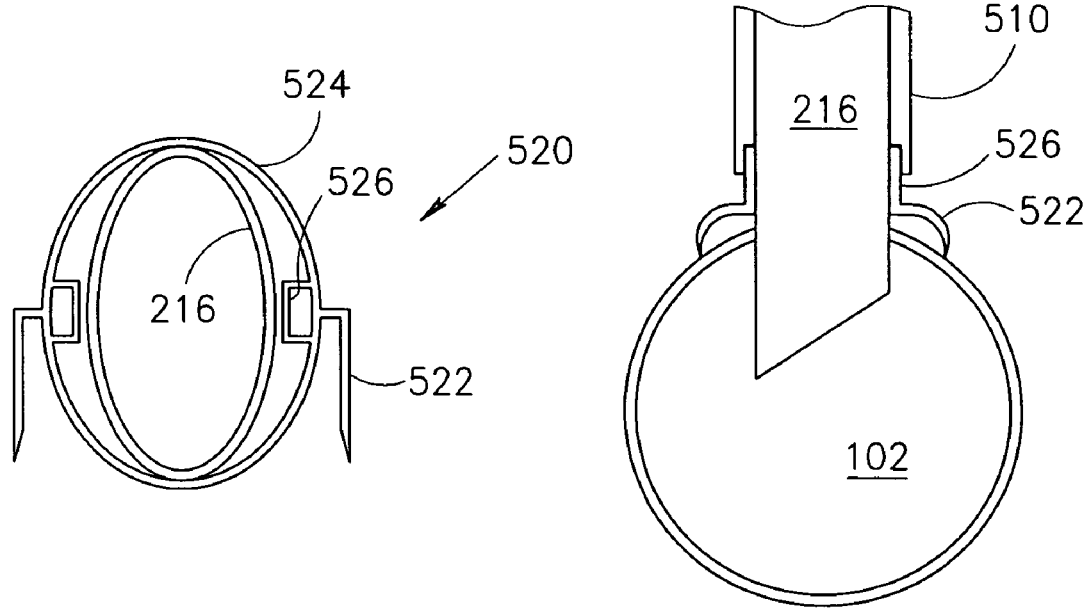
FIG.11A
FIG.11B
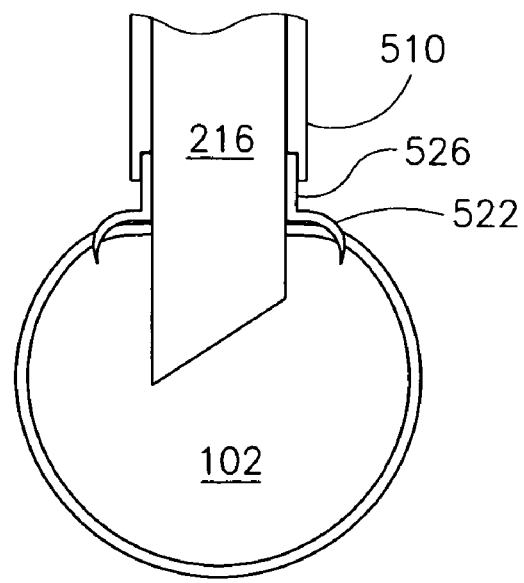
FIG.11C

VASCULAR CLOSURE DEVICE

RELATED APPLICATIONS

This application is the U.S. national phase 371 of PCT application No. PCT/IL99/00674, filed Dec. 9, 1999, which is a continuation-in-part of U.S. Application No. 09/701,523, filed on Nov. 28, 2000, which is the U.S. national phase 371 of PCT application No. PCT/IL99/00285, filed on May 30, 1999, and is a continuation-in-part of U.S. application No. 09/701,531, filed on Nov. 28, 2000, which is the U.S. national phase 371 of PCT application No. PCT/IL99/00284, filed on May 30, 1999, and is continuation-in-part of U.S. Application No. 09/936,806, filed on Sep. 17, 2001, which is the U.S. national phase of PCT application No. PCT/IL99/00670, filed on Dec. 8, 1999.

FIELD OF THE INVENTION

The present invention relates to vascular devices and especially to sealing vascular incisions.

BACKGROUND OF THE INVENTION

There are many medical procedures in which a tube is temporarily inserted into- or out of- a blood vessel. One particular example is the use of a heart-lung machine during heart surgery. A first cannula is inserted into the aorta to return blood after it was oxygenated by the heart-lung machine. One or more second cannulas are inserted into the vena cava or the right atria. When the heart surgery is completed, the two cannulas are removed and the holes in the vena cava and aorta are closed using a "purse-string" suture, in which a single thread is stitched to surround the hole and then pulled tight (like a purse-string) to close the hole. Performing this suture requires skill and practice. In addition, it may be difficult to perform the suturing in a key-hole procedure or in other types of surgery where there is limited access to the wound site. Typically, the suture is attached as soon as the cannula is inserted into the body.

Another type of temporary tube insertion occurs during a failed anastomosis procedure. If the joining of two blood vessels fails, the point at which an opening (if any) was formed in one of the blood vessels, must be sutured shut, also possibly using a purse string.

Vascular ports, for example for the introduction of a catheter into a femoral artery, are known. Once the procedure is completed, the port is usually removed and the hole formed by the port is either sutured or closed using manual pressure. These ports are generally applied through the skin or a small incision and remain mostly outside the body.

U.S. Pat. No. 5,478,354, the disclosure of which is incorporated herein by reference, relates to a the field of closing non-linear surgical incisions, in fascia and/or skin, using a single fastener and describes various devices for closing such non-linear surgical incisions.

SUMMARY OF THE INVENTION

An aspect of some preferred embodiments of the invention relates to a closure device for sealing a vascular incision. In some embodiments, the device may also function as an access port for the vessel. In other embodiments, the device is provided as an add-on to an existing port or is brought in after the fact to seal a hole remaining when the port is removed. In some embodiments, the device is self deployed, such that little or no user intervention is required to seal the device. In other embodiments, the device is deployed manually. Preferably, but not necessarily, the device is suture-less.

An aspect of some preferred embodiments of the invention relates to a vascular closure device adapted for sealing femoral and/or other oblique ports. In one embodiment, the device is applied from outside the blood vessel. In another embodiment, the device is applied from inside the blood vessel. In yet another embodiment, the device is applied from both the inside and the outside of the blood vessel.

An aspect of some preferred embodiments of the invention relates to safety. In a preferred embodiment of the invention, if a suitably equipped port is accidentally retracted from a blood vessel, a closure device on the port seals the remaining hole and prevent blood leakage.

An aspect of some preferred embodiments of the invention relates to a low profile closure device. In a preferred embodiment of the invention, when the hole closing is completed, there is substantially no change in the inner and/or outer profile of the sealed blood vessel at the previous hole location. In some cases, a small bump will remain.

An aspect of some preferred embodiments of the invention relates to a closure device which, when sealing a hole in a blood vessel, aligns at least one, and preferably more layers of a vascular tissue of the blood vessel. Layers which may be matched, include the endothelial layer (inside), the adventizia layer (outside) and one or more of the muscular layers in-between.

In a preferred embodiment of the invention, the type of closure device used depends on the type of vascular tissue. For example, an incision in thin tissue, such as of a femoral artery is sealed by compressing the two sides of the incision against each other. In thicker tissue, such as an aorta, a radially compressive closure may be used. In other embodiments, this distinction between tissue types is not made.

An aspect of some preferred embodiments of the invention relates to a method of manipulating and releasing an implanted device, in which a wire that engages the device is used to retract the device against a base, to deform the device. Then, the device is attached to a body structure and one end of the wire is released, to release the device. The device may be plastic, shape-memory, elastic and/or superelastic. In some of these types of materials the device will return to an un-deformed state after it is released, thereby manipulating the tissue. Preferably, the device is a hole closure device. It should be noted that in a hole closure procedure, typically only one device is to be implanted, so the use of a wire, which will need to be re-threaded for another procedure (if at all) is not generally a problem. Alternatively, the device is an anastomosis connector, including spikes that are bent into a desired configuration using the above method. Alternatively, the device is a surgical staple, which is opened, or closed using such a wire or by a suture mechanism.

An aspect of some preferred embodiments of the invention relates to a self-sealing anastomotic device. In a preferred embodiment of the invention, if an anastomosis cannot be or is not completed, the device seals an opening in the vessel to which the device is connected. In a preferred embodiment of the invention, the device seals the opening by forcing the lips of the opening against each other or against a part of the device. Alternatively, the device seals the opening by forcing portions of the device against each other. In some embodiments of the invention, the anastomosis device severs a portion of one of the vessels of the anastomosis, for example an "end" vessel in an end-to-side anastomosis. Alternatively or additionally, the device, when it seals the opening, engages a larger portion of the blood vessel to which it is attached, to form a seal. In an exemplary embodiment, an anastomotic device includes a collar portion which is elastically disposed to collapse and seal the opening. A second collar is provided over the first collar to maintain its shape. If the connection fails, the second collar is removed and the anastomotic device seals.

Alternatively to an integral device, the opening sealer may for an element which is brought over an existing anastomosis device or blood vessel, to seal the opening in the device or the blood vessel. In one example, the element comprises a collapsing ring which compresses the diameter of an anastomosis device and/or a blood vessel. Possibly, the element also severs a portion of the blood vessel, leaving only a stub, which stub is sealed. In some embodiments a double seal is formed, one at the severing location and one nearer to the blood vessel.

There is thus provided in accordance with a preferred embodiment of the invention, a device for sealing a hole in a blood vessel, comprising:
  a ring;
  a plurality of spikes extending from said ring, towards a center of said ring and to first direction along an axis of said ring, said spikes being adapted for engaging a blood vessel;
  a plurality of tabs extending substantially radially from said ring,
  wherein rotating said tabs around said ring distorts said ring such that said spikes are rotated in a same direction as said tabs. Preferably, said device is comprised of a super-elastic material. Alternatively or additionally, said spikes are curved.

In a preferred embodiment of the invention, said tabs and said spikes are attached in pairs of one spike and one tab at a plurality of locations along the circumference of said ring. Alternatively, said tabs and said spikes are not attached at same locations along the circumference of said ring.

In a preferred embodiment of the invention, said spikes are evenly arranged around the circumference of said ring. Alternatively or additionally, said ring has a resting state in a shape of a circle. Alternatively, said ring has a resting state in a shape of an ellipse with a large ratio between the length of its two axes. The ring may be smooth or it may be undulating, for example in the form of a sine wave. Preferably, said spikes are arranged on opposing sides of said ellipse.

In a preferred embodiment of the invention, said spikes are substantially perpendicular to a plane defined by said ring. Alternatively, said spikes are slanted in a same direction relative to a plane defined by said ring.

In a preferred embodiment of the invention, said ring is radially expandable. Alternatively or additionally, said plurality of spikes comprises two spikes. Alternatively, said plurality of spikes comprises three spikes. Alternatively, said plurality of spikes comprises five spikes. Alternatively, said plurality of spikes comprises six spikes.

There is also provided in accordance with a preferred embodiment of the invention, a cannula having mounted thereon a device as described above. Preferably, said cannula comprises an aortic cannula. Alternatively, said cannula comprises a femoral cannula.

There is also provided in accordance with a preferred embodiment of the invention, a vascular port having mounted thereon a device as described above.

There is also provided in accordance with a preferred embodiment of the invention, a vascular access kit comprising:
  a sterile container for the kit;
  a vascular port; and
  a suture-less hole closure device adapted to fit over said port. Preferably, said hole closure device is as described above.

There is also provided in accordance with a preferred embodiment of the invention, a vascular access kit comprising:
  a sterile container for the kit;
  a vascular port; and
  a suture-less hole closure device adapted to fit through said port. Preferably, the kit comprises a device holder adapted to fit through said port and adapted for holding said device. Optionally, said device comprises a clip.

In a preferred embodiment of the invention, the kit comprises:
  an outer element adapted to mount over said port; and
  a base for a hole closure device adapted to cooperate with said hole closure device to seal a hole remaining in said vessel when said port is removed.

There is also provided in accordance with a preferred embodiment of the invention, a set of a hole closure device and a delivery system, comprising:
  a delivery system comprising:
    an inner rod;
    at least one peg extending from said rod and axially movable relative to said rod;
  a device comprising:
    a base;
    a curved spike extending from said base in a same general direction,
  wherein, said peg is engaged by said device, in a resting configuration, between said base and said curved spikes and wherein said curved spikes are configured such that when said peg is retracted from said base, said peg causes said spikes to rotate, around a line perpendicular to said retraction. Preferably, said system comprises a tube adapted to pass over said inner rod and advance to apply force against said spikes in a direction that causes them to rotate opposite from said peg retraction. Alternatively or additionally, said device is plastically deformed by said retraction of said peg. Alternatively or additionally, said spikes are mounted on protrusions from said base.

There is also provided in accordance with a preferred embodiment of the invention, a two part hole closure device for a blood vessel, comprising:
  a base part comprising:
    a skeleton; and
    a plurality of spike receptacles disposed around said skeleton;
  a spike part adapted for contact with blood flow comprising:
    a plurality of spikes having tips and adapted for fitting in said plurality of receptacles, wherein said spikes are curved such that when said spike part is inserted in said base part, said spike tips are in a plane substantially parallel to said base part.

There is also provided in accordance with a preferred embodiment of the invention, a device for implanting a clip having a base and at least two spikes inside a blood vessel, comprising:
  an elongate rod adapted to engage said base of said clip at its end;
  a tube fitted over said rod and slideable with respect to said rod, wherein said rod and said tube are deigned to cooperate with a particular clip, such that when said clip is engaged by said rod and said tube is advanced towards said clip, said spikes of said clip are spread apart. Preferably, said rod includes at least one cable guide and wherein a cable is provided through said cable guide to maintain said clip in place. Preferably, said cable guide comprises a lumen in said rod. Alternatively, said cable guide comprises a groove along said rod.

In a preferred embodiment of the invention, said tube comprises at least one notch for engaging said clip.

There is also provided in accordance with a preferred embodiment of the invention, a method of implanting a clip from inside a blood vessel, comprising:

providing a clip having at least two spikes inside the blood vessel;

spreading apart the spikes and maintaining them in said spread configuration;

retracting said clip such that said clip engages said blood vessel on either side of a hole in said vessel; and releasing said clip. Preferably, releasing said clip comprises releasing at least one end of a thin cable that holds said clip in a loop of said cable. Alternatively or additionally, said method includes releasing said spikes from said spread configuration after said retracting.

There is also provided in accordance with a preferred embodiment of the invention, a method of controlling a super-elastic device using a wire, comprising:

engaging said device between a loop in a wire and a holding surface;

applying a force away from said holding surface to distort said device;

deploying said device in a desired location; and releasing at least one end of said wire thereby freeing said device. Preferably, the method comprises ceasing said force, thereby allowing said device to relax. Alternatively or additionally, said device comprises a clip.

There is also provided in accordance with a preferred embodiment of the invention, a device for sealing a hole, comprising:

an undulating ring having a plurality of inwards pointing portions and a plurality of outwards pointing portions; and a plurality of spikes, wherein said spikes extend towards a center of said ring from portions of said ring intermediate said inwards and said outwards pointing portions. Preferably, said device is formed of a single piece of sheet metal, without heat treatment after forming. Alternatively or additionally, said device is super-elastic.

BRIEF DESCRIPTION OF THE DRAWINGS

The invention will be more clearly understood by reference to the following description of preferred embodiments thereof in conjunction with the figures, wherein identical structures, elements or parts which appear in more than one figure are labeled with the same numeral in all the figures in which they appear, in which:

FIGS. 1H and 1I illustrate a port having two sets of spikes, in an open and a closed configurations, respectively, in accordance with a preferred embodiment of the invention;

FIGS. 1J and 1K illustrate a port sealer in an open and a closed configuration, respectively, in accordance with a preferred embodiment of the invention;

FIGS. 1L and 1M illustrate two alternative methods of manufacturing the port sealer of FIG. 1J;

FIGS. 11A–11E illustrate a femoral hole closure device and deployment thereof, in accordance with a preferred embodiment of the invention;

DETAILED DESCRIPTION OF PREFERRED EMBODIMENTS

Figure 1A:
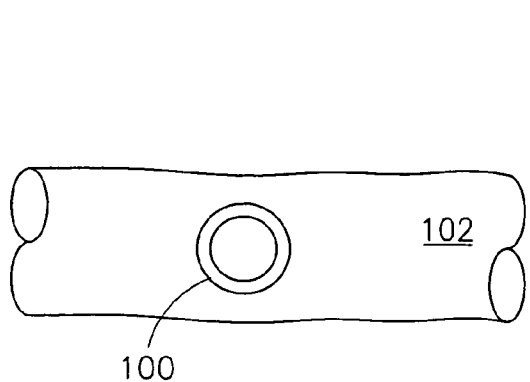
FIGS. 1A–1D illustrates a self-sealing vascular port, in accordance with a preferred embodiment of the invention.
Figure 1B:
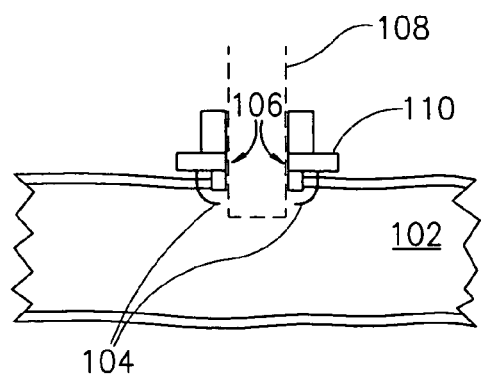
Figure 1C:
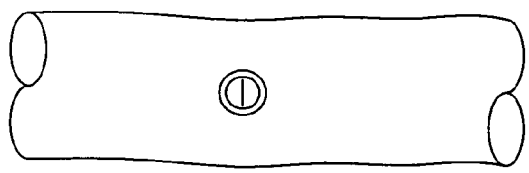
Figure 1D:
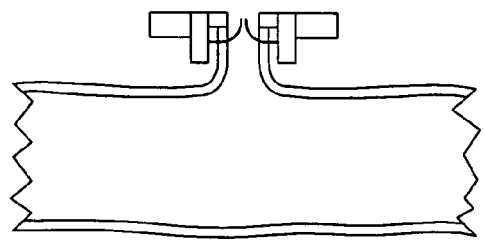

FIGS. 1A–1D illustrate a self-sealing vascular port 100 in a vessel 102, in accordance with a preferred embodiment of the invention. FIGS. 1A and 1B illustrate a top view and a side cross-sectional view (respectively) of port 100, in an open configuration and FIGS. 1C and 1D illustrate port 100 in a sealed configuration. In the following figures, some changes have been made for clarity. For example, some of the "seals" are shown partly open, the degree of eversion is exaggerated in some figures, the length of spikes is sometimes exaggerated and the amount the spikes protrude from blood vessels is sometimes exaggerated. In particular, although a 90° eversion is shown, for example in FIG. 1B, a smaller eversion or no eversion can also be accomplished. In the exemplary embodiment of FIG. 1, port 100 comprises a ring 110 having a plurality of spikes 104 to engage vessel 102. FIG. 1B shows port 100 being open and a tube 108 (dotted line) inserted in the opening of the port. In FIG. 1D, tube 108 is removed and port 100 changes configuration to become sealed, so no blood can exit from vessel 100. In the embodiments of FIGS. 1A–1D, ring 110 rotates around its median axis, which axis is generally completely enclosed by the body of the ring, so that spikes 104, which engage vessel 102, urge portions of vessel 102 against each other. In this type of distortion, the ring does not move or rotate relative to the main axis (which is perpendicular to the blood vessel), but each circular cross-section of the ring rotates around the center of the cross-section. Preferably, an intima-to intima seal is achieved, however, this is not required in all preferred embodiments of the invention. In a preferred embodiment of the invention, once the port is sealed, the port remains in the body, possibly indefinitely.

Various mechanisms may be utilized to cause the change in configuration of port 100, including passive mechanisms, in which the port changes configuration by itself, active mechanisms in which the force is applied to the port and triggered mechanisms, in which a trigger is released by some means and the port then passively (or as a result of an outside force) distorts.

Passive mechanisms include for example, elasticity, super-elasticity and shape memory mechanisms. In one example, port 100 is pre-stressed to desire to achieve the configuration of FIG. 1D. However, as long as a tube 108 is inserted therein, this configuration cannot be achieved. Once the tube is removed, port 100 returns to the sealed configuration. In another example, the pressure of blood inside vessel 102 or the elasticity of vessel 102 causes configurational changes in port 100 (illustrated below).

Active mechanisms include, for example, applying force to distort port 100. In one example, the force is applied by tube 108 during its removal. During which removal, the tube, if it engages the port, can, for example, plastically distort the port. In another example, the force is applied using a second device, for example a surrounding balloon (shown in FIG. 6D, below) which distorts the port and/or squeezes it shut. Such a surrounding balloon may form part of the port, such that the inflated balloon (possibly permanently inflated) maintains the port sealed. Alternatively the balloon may be used to plastically distort the port, after which distortion the balloon may be removed. Other types of forces can also be used to distort the port, including direct mechanical compression, for example using a pliers-like device.

Triggered mechanisms, include, for example a pin, which restrains the port from sealing. When the pin is removed, the port passively (or actively) distorts and seals (shown in FIG. 2, below). Alternatively, the removal of the pin allows the port to be distorted by an external balloon. In the case of FIG. 2, if the port does not distort by itself, the removal of the pin does make active distortion of the port easier (e.g., requiring less force).

Figure 1E:
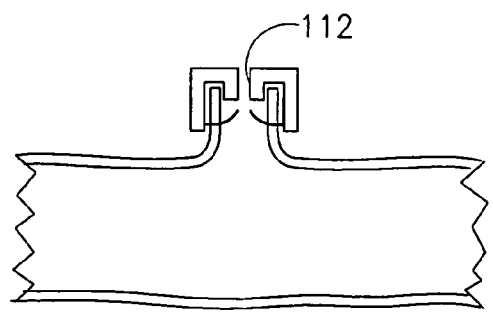
FIGS. 1E–1G illustrate various sealing mechanisms, in accordance with preferred embodiments of the invention.
Figure 1F:
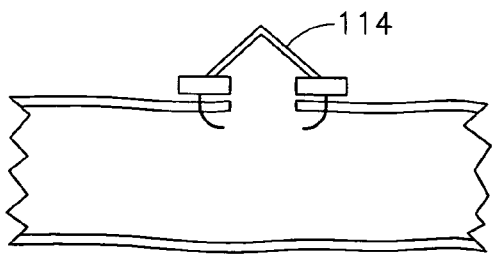
Figure 1G:
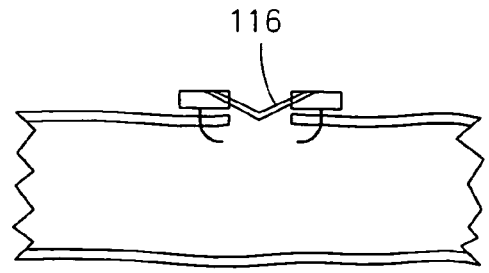
Figure 1N:
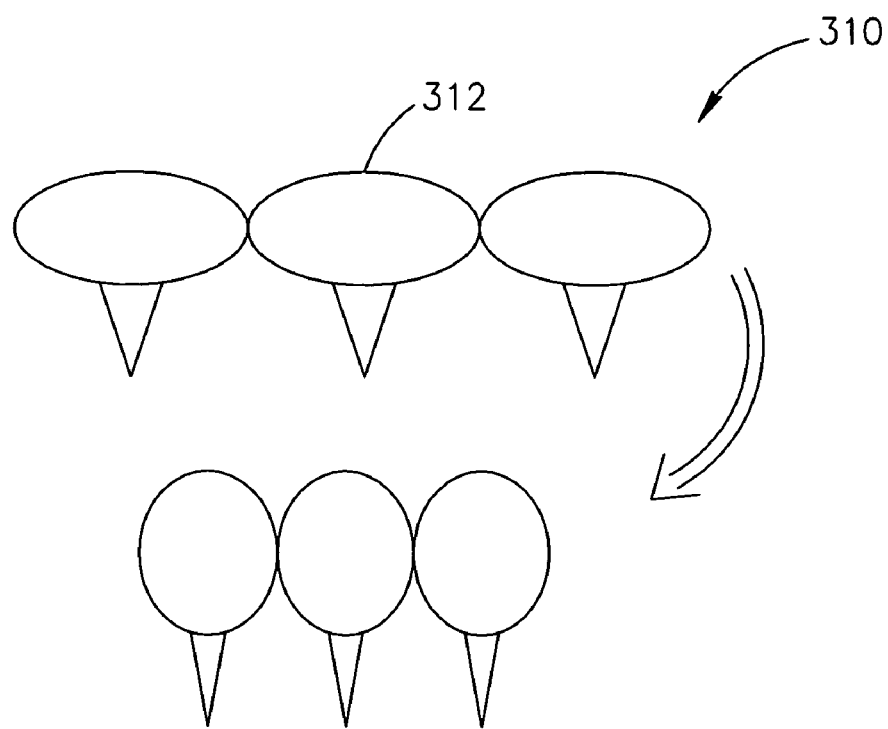
FIGS. 1N and 1O illustrate variations on the port sealer of FIG. 1J, in accordance with preferred embodiments of the invention.
Figure 8A:
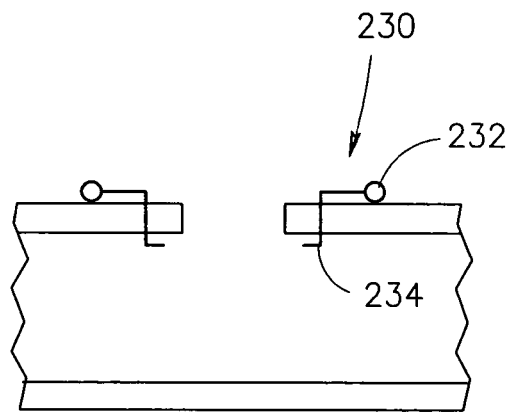
FIGS. 8A and 8B illustrates a hole sealer in which it is possible to avoid any contact between the sealer and the blood flow, in accordance with a preferred embodiment of the invention.
Figure 8B:
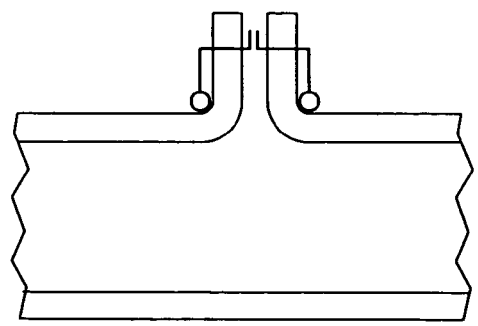
Figure 8C:
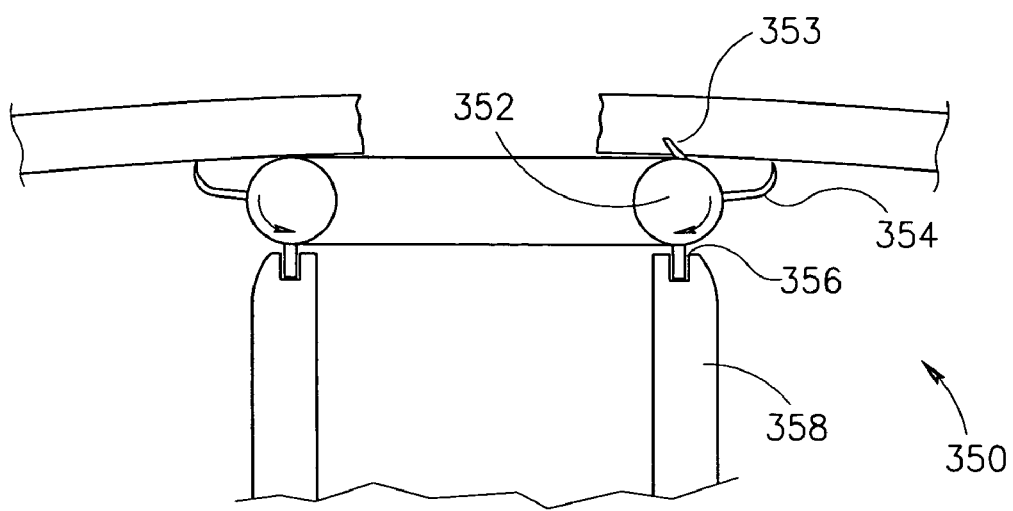
FIGS. 8C and 8D illustrate another hole sealer in which contact between the sealer and blood can be avoided, in accordance with a preferred embodiment of the invention.

As can be appreciated, various types of distortions of port 100 may be utilized, including the following (and combinations of the following) types of distortion:

(a) symmetric distortions, in which a similar distortion is applied to several parts of the port, for example a rotation around ring 110, an example of which is shown in FIG. 1N, below;

(b) asymmetric distortion, for example squeezing the port from a circular shape to an elliptical shape;

(c) rotational distortion, for example median-axis distortion as shown in FIGS. 1A–1D and in Figs. in FIGS. 8B and 8C;

(d) iris-type distortion, in which the port, or at least parts of it collapse inwards like an iris;

(e) partial distortion, in which part of port 100 distorts and part remains stable, for example when the spikes are not distorted but their base is, or vice versa;

(f) various types of distortion of outlines, for example from an arc to a sine wave (FIG. 1J);

(g) spiral distortion, for example in FIG. 2, where the "coils" of the port tighten, thereby reducing its inner lumen; and (h) varying amounts distortion, like a star distortion shown in FIG. 1M, where only spiked portions of the ring distort, and other portions do not (or distort less) or vice-versa, with at least some of the spiked portions not distorting.

FIG. 1D illustrates an embodiment where the sealing of port 100 is achieved by portions of vessel 102 being urged against each other. FIG. 1E illustrates an alternative embodiment of the invention, in which port 100 includes an inner lip 112, which may be formed of one or more sections. When port 100 distorts, lips 112 press against each other (as shown in the Fig.) or against vessel 102, to form the seal of port 100.

FIG. 1F illustrates a port in which an external lip 114, formed for example of resilient rubber, creates a seal when an inserted tube is removed. In this example, substantially no distortion of port 100 is required.

FIG. 1G illustrates a port having an internal lip 116, in which the seal of the lip is enhanced by the internal pressure of vessel 102. Although FIG. 1G utilizes a mechanism similar to that of FIG. 1F, in which port 100 does not substantially distort, a same type of seal can be realized if port 100 distorts as in FIG. 1D (or in FIGS. 8C and 8D), but inwards, rather than outwards. In this variation, once lip 116 reaches the configuration shown in the Fig., the lip preferably cannot be pushed out of the blood vessel, due to a ratchet effect of the lip pressing against itself (or it may be formed of leaflets which press against each other) and/or due to a radius reduction (as in FIG. 8D) of the port, during the distortion.

The embodiment of FIG. 1G illustrates an optional feature of some preferred embodiments of the invention, in which the same port can be reused for inserting a second tube 108 from outside the blood vessel, by pressing the tube against lips 116. Thus, port 100 can be a single use port, for example for by-pass surgery, where, a heart-lung machine cannula is usually only inserted once. Alternatively, port 100 can be a multiple use port, for example during surgical procedures in which a plurality of catheters are inserted into or out of a blood vessel. Some types of ports described herein can also be used as permanent ports, such as for dialysis patients, however, these ports are especially suitable for short-duration uses, such as minutes, hours, days or weeks (such as 1, 2, 3 or 5 weeks), in which the "trouble" of removing the port and sealing the hole can be averted by some of the embodiments described herein.

Port 100, as described above can be designed to have only one set of spikes 104. When the port is distorted, all of the spikes move, as a group, to seal the port. FIGS. 1H and 1I illustrates an embodiment in which a port 118 includes at least two sets of spikes: a set 104 and a set 119, which sets move independently, with one set coming together to close the hole and another set 119 staying is place in moving in a different direction. A benefit of this type of multi-spike configuration is that the port maintains a fixed reference point relative to vessel 102, as well as or instead of relative to the sealed hole. Also, such a multi-spike embodiment may be useful for de-coupling the sealing of the port from elastic and/or other tensions in vessel 102. Various mechanisms may be used for changing between the configurations of FIGS. 1H and 1I, for example, super elastic expansion of the base of the port or a balloon inflation mechanism such as in FIG. 6D.

In a preferred embodiment of the invention, once the utilization of port 100 is completed, port 100 is sealed. In a preferred embodiment of the invention, port 100 remains in the body. In some cases, it may be desirable to remove port 100, however, this is generally not required.

FIGS. 1J and 1K illustrate a port closing device 300, in accordance with a preferred embodiment of the invention. the device comprises a ring 304 having a plurality of spikes 302 attached thereto. In FIG. 1J the port closer is in an expanded (open configuration). The port closer is advanced in this configuration until the spikes engage a blood vessel. Then, ring 304 is distorted (as shown in FIG. 1K), so that spikes 302 move towards each other and pinch between them portions of the blood vessel, sealing the lumen of the port closer. Ring 304 is preferably formed of an elastic, super elastic and/or shape memory material, so that it is pre-disposed to collapsing in the absence of a restraint (such as a tube 108 inside of it). However, as described herein, the method of collapsing can include plastic deformation of the device by an external force or a combination of plastic- and other types of deformation.

FIG. 1L illustrates a method of manufacturing device 300, by cutting it out of a tube 306, for example using a wire EDM, a laser or a water jet. FIG. 1M illustrates an alternative method of manufacture, in which device 300 is cut out of a sheet 308. In some embodiments, the device is machined after it is cut, for example to remove burs or to roughen the surface. In a particular example, ring 304 is machined or otherwise worked to have a circular cross-section rather than a rectangular one.

FIG. 1N illustrates a portion of a device 310 which is a variation of device 300. The portion shown is a part of "ring" 304 and spikes attached thereto. Device 310 has ring 304 replaced by a series of distortable geometric shapes (cells) 312, such as ellipses (shown) or parallelograms. When the shapes are distorted, for example form that of a horizontal ellipse to that of a vertical ellipse, the circumference of the device is reduced, bringing the spikes closer together.

Figure 1O:
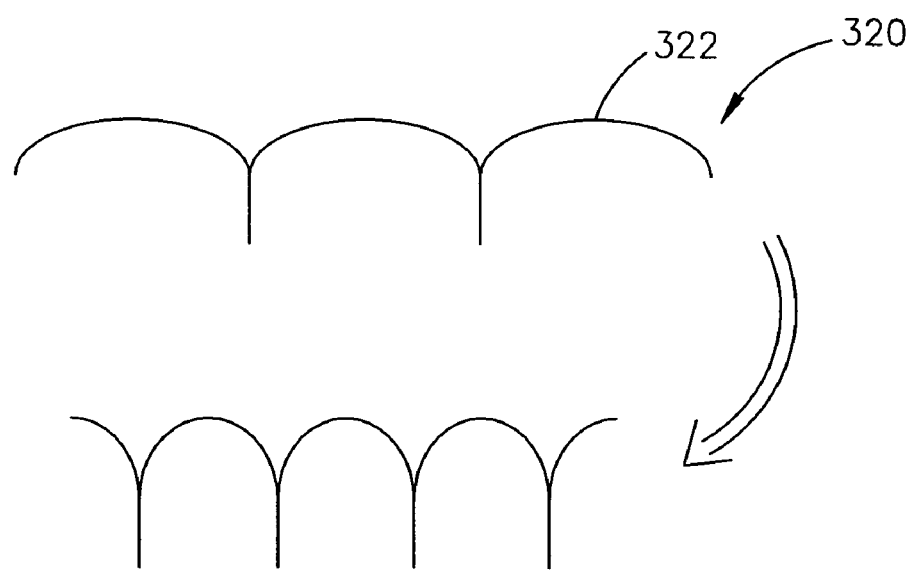

FIG. 1O illustrates a portion of a device 320 which is a variation of device 300, in which variation device 320 has ring 304 replaced by a series of arcs 312, which arcs can distort to have a greater curvature (and a smaller overall device circumference).

It should be noted that although the ring (or its replacement-variations) are shown as having a cross-section which is substantially perpendicular to the blood vessel surface, the ring-cross-section can be at other angles to the vessel, for example parallel to the vessel surface. Further, this angle can vary along the device or as a function of the deployment configuration of the device.

Figure 2A:
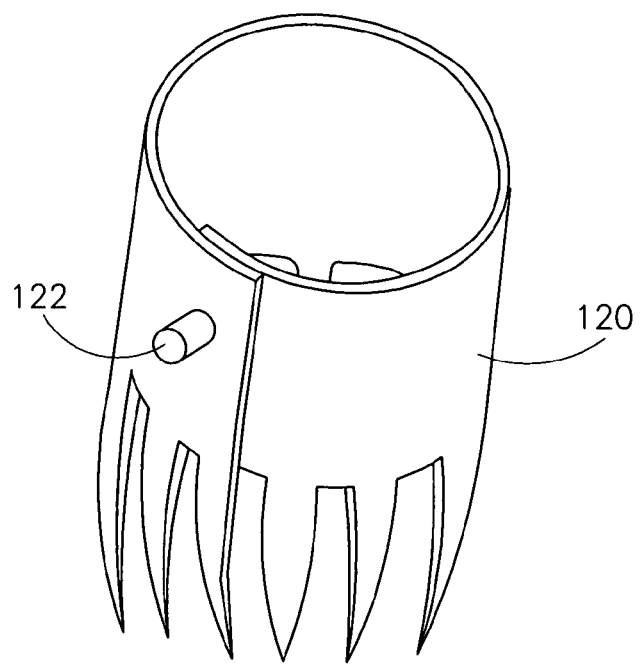
FIGS. 2A and 2B illustrate a port including a pin, in which the port seals, once the pin is removed, in accordance with a preferred embodiment of the invention.
Figure 2B:
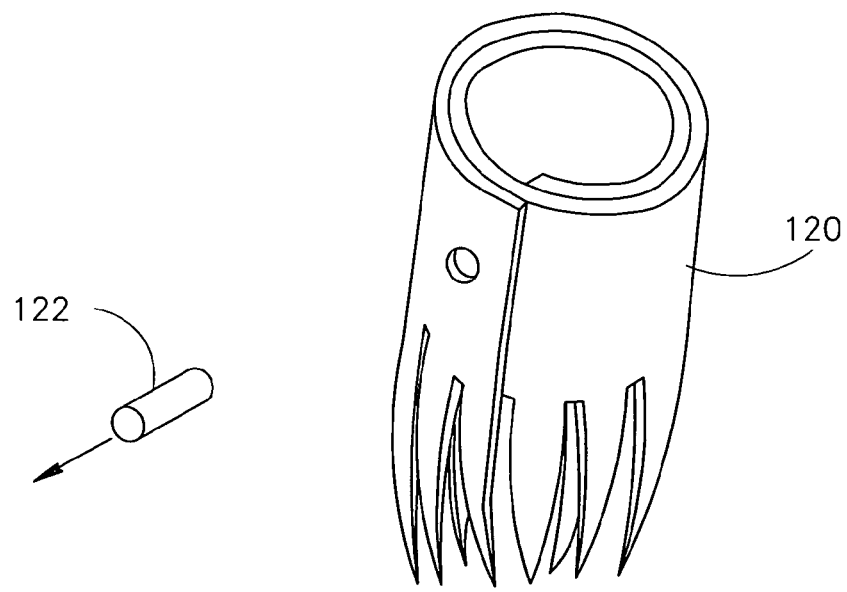

FIGS. 2A and 2B illustrates a port 120 including a pin 122. Once pin 122 is removed, port 120 seals at once, or seals once an internal tube is removed, and cannot be reopened. The sealing is preferably achieved by urging portions of the vessel which are engaged by the spikes of the port, towards each other. Alternatively, other methods of sealing the port, such as by applying an external force, may be used. Alternatively to a pin, the triggering of the sealing of port 120 may be achieved using a drawstring. Possibly, a time delay mechanism is used, to assure that all ports seal after a time, such a time-delay mechanism can include a bio-absorbable pin, which, when it is sufficiently absorbed or softened by being in the body, allows the port to distort.

In a preferred embodiment of the invention, port 100 includes a layer of clot inducing material outside the blood vessel, to induce clotting in any blood which escapes the seal. Such a layer may be provided as a coating on port 100. Alternatively or additionally, such a layer is provided during or after the deployment of port 100. Alternatively or additionally, port 100 includes an adhesive layer, to glue the lips of the port to each other and/or to the lips of vessel 102 at the hole that the port creates.

Figure 3:
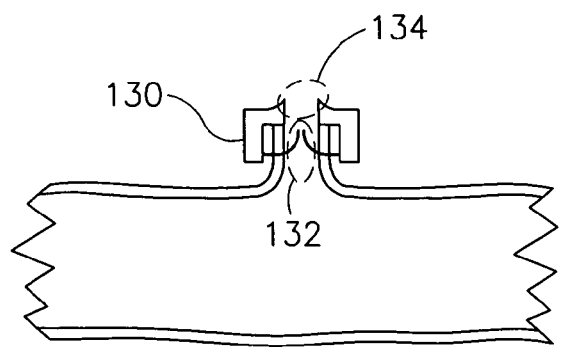
FIG. 3 illustrates a port having a two layer seal, in accordance with a preferred embodiment of the invention.

FIG. 3 illustrates a port 130 having a two layer seal, for example to provide added security against leakage. In the example of port 130, a first seal 132 is provided by urging portions of vessel 102 against each other. A second seal 134 is provided by urging outer lips of port 130 against each other.

As illustrated in FIG. 1A, the port includes a circular opening. However, in some embodiments of the invention, other shapes of openings may be useful, for example, ellipses, multiple holes, such as provided by a figure "8" or a key-hole cross-section and polygonal holes (for example triangular holes and square holes). The profile of the hole may be square, conical, hourglass or any other shape, for example by suitably forming the lips of port 100 or ring 110. Different port shapes are especially useful when the port is used for closing up a preexisting tear or other lesion of the vessel, in allowing the device to be matched to the lesion. In some embodiments of the invention, the inner lumen of the port is perpendicular to that of the blood vessel. In others, it may be parallel or at a different angle, for example less than 70°, less than 50° or less than 40°. Alternatively or additionally, the cross-section of the lumen is substantially the same as the outer cross-section of the port. Alternatively, the port may have a different shape and/or have a considerable thickness, so that the cross-sections are not the same.

The lips of the port may be formed of a continuous ring. In some embodiments, the lips are formed of a plurality of overlapping or non-overlapping leaflets. The overlapping may be at the sides of the leaflets and/or at the tips of the leaflets. In some preferred embodiments of the invention, a leaflet includes one or more crevices and/or protrusions to engage other leaflets and aid in forming the seal.

In a preferred embodiment of the invention, the port is formed of hard material, such as a metal, for example stainless steel or an NiTi alloy or a plastic. Alternatively or additionally, the port is formed of a soft material, such as a silicon rubber. In various preferred embodiments of the invention, the port, or parts thereof, exhibit elastic, super elastic, plastic and/or shape memory properties. In some preferred embodiments of the invention, the port is formed of a rigid frame which is coated with a soft layer, such as silicon rubber. The frame preferably provides the ability for the port to passively or actively distort and the silicon preferably provides a resilient seal and/or a pressure distributing means.

In some preferred embodiments of the invention, the port is formed of bio-absorbable materials, preferably, so that after a time the port dissolves or is otherwise broken down, completely, or at least in part. Alternatively, the port device may be made of other materials, for example, stainless steel, titanium alloys, such as Nitinol, and/or various plastic materials, possibly non-absorbable.

A PCT application titled "Methods and Devices for Vascular Surgery", filed on May 30, 1998 and having PCT application number PCT/IL99/00284, the disclosure of which are incorporated herein by reference, describes various anastomotic connectors. Some of these anastomotic connectors include a mechanism for engaging a blood vessel, entering (or exiting) the blood vessel, and/or maintaining a hole in a blood vessel. In a preferred embodiment of the invention, these mechanisms are utilized for providing and/or using a self-sealing port, as described herein.

One or more of the following issues are preferably taken into account when designing and/or selecting a device for sealing a port. These issues are listed in a general order corresponding to the steps of using such a device.

A first issue is bringing the port to the blood vessel. In a preferred embodiment of the invention, a port is brought to a blood vessel using a catheter (inside the blood vessel) or an endoscope (from outside the blood vessel). In some cases, the port is used in a surgical procedure in which the access to the blood vessel is a keyhole surgical wound or a standard surgical wound. Preferably, the port is formed of an elastic material so that it can be radially and/or axially compressed during the provision of the port.

A second issue is engaging the blood vessel by the port. In a preferred embodiment of the invention, the port includes spikes which, can be selectively bent (or released) when the port is brought into contact with the blood vessel, thereby engaging the vessel. Alternatively or additionally, the port may be sutured to the vessel, preferably using a minimally invasive technique, for example as described in PCT publication WO 98/42262, the disclosure of which is incorporated herein by reference. Alternatively or additionally, the engaging is integrated with the hole making, described below. In a preferred embodiment of the invention, the port is provided in a first undistorted configuration. When the port is placed against the vessel, the port (or part of it) is distorted, thereby allowing the spikes to engage the vessel. Sealing the port is preferably achieved by further distorting the port. Alternatively, in some configurations, if the port is distorted using a force opposite to the one which caused the distortion in the first place, the port seals, rather than being removed (for example utilizing a structure such as in the embodiments of FIGS. 1H and 1I). In some preferred embodiments of the invention, the blood vessel is engaged using a suction source provided at port 100.

Engaging the blood vessel may be achieved by various mechanisms for folding, extending and bending spikes while deploying an implantable device. As described in the above PCT application of even date, spikes can be bent using many mechanisms, including elasticity, cantilevering, twisting and bending by force.

A third issue is forming the hole in vessel 102. In a preferred embodiment of the invention, the hole is formed using a sharp tip or a knife, possibly provided using the same means as the port, and/or provided through the opening in the port. Alternatively, the port itself, for example in a first, distorted configuration, has a sharp tip which forms the hole. For example, in the embodiment of FIG. 1J, if the device is provided to the vessel in a collapsed configuration with the spike tips overlapping (forming a general shape of a cone), the hole may be formed by expanding the device after the cone pokes into the blood vessel. Once the device is expanded, a tube may be placed in the hole and the device retracted and then advanced, so that the spikes can engage the vessel, individually. Alternatively, a device as shown in the above referenced PCT application of even date may be used, in which the spikes first cut the hole and then distort or move to engage the blood vessel. Alternatively or additionally, to cutting, a hole may be formed using a punch, possibly utilizing the body of port 100 as part of the punch, for example as the punch's anvil.

A fourth issue is expanding a hole in vessel 102 to the desired size of the port. In some cases, the hole is formed at its full size. However, in other cases, the formed hole is small and needs to be expanded. In a preferred embodiment of the invention, the hole is expanded using a balloon which is inflated in the hole. Alternatively or additionally, the hole is expanded by causing spikes 104 which engages vessel 102 to travel away from each other, thereby expanding the hole. It should be appreciated that the engagement of vessel 102 may possibly proceed in several steps or may occur only after the hole is formed. In one example, spikes 104 engage vessel 102 only after the hole is formed and then expanded using a balloon. A different set of spikes (if any) may be used for the primary engagement of the vessel, in which engagement the port is coupled to the vessel.

A fifth issue is maintaining the hole in vessel 102. In some cases, for example in some types of passive ports, the port, if left alone, seals the port. The hole is preferably maintained by restraining the port from closing, for example by inserting tube 108 therethrough. Alternatively, the port comprises a bi-stable configuration, with the stable states being "open" and "closed". A bi-stable element is described in PCT publication WO 98/32412, the disclosure of which is incorporated herein by reference. In this PCT publication, a stent with two stable radii is described. A similar configuration as the stent, but including spikes at one end thereof (as in FIG. 2, for example) can be used to provide a port and then seal it, in accordance with a preferred embodiment of the invention. The spikes engage the blood vessel when the port is changed to a smaller diameter stable state the spikes move towards each other urging the lips of the hole in the vessel against each other and sealing the hole. The above PCT also describes a bi-stable valve. However, unlike the valve described there, in the present embodiment, the bi-stable element is used to selectively reduce the radius of the entire lumen, for the purpose of sealing the lumen. In the PCT publication, the bi-stable element is either used to compresses a stent (without sealing the lumen and without causing spike-engaged portions of the vessel to abut) or to move a valve element against a specially formed valve.

In the bi-stable embodiment of present invention, once the port is in the open state, it will tend to stay open, unless the port is shifted to the closed state. Alternatively to a bi-stable mechanism, a ratchet based mechanism may be used, either to create a "normally open" port or a "normally closed" port. Once the port is in one state, the ratchet latches and the port can change configuration only by application of a large force or by releasing the latch (for example a pin as described in FIG. 2).

A sixth issue is distorting the port or parts thereof. The above PCT application of even date describes various mechanisms of distorting an implant, including shape-memory, balloons, including balloons or other distorting tools, possibly with fingers for pressing against particular points on the port structure, and bi-stable structures. Any of these mechanisms may be applied towards constructing a port in accordance with a preferred embodiment of the invention. It should be appreciated that different parts of the port, for example the ring and the spikes, or individual spikes, may be distorted in different ways and by different amounts. Further, a same part of the port may be distortable in more than one way.

A seventh issue is how much of the port remains in contact with the blood flow after the port is sealed. As can be seen in various embodiments described herein, the contact area can be large, for example the entire size of the hole. Alternatively it can be small, for example is the hole is shrunken by the closure of the port. It can be minuscule, for example if only small portions of the spikes remain in the blood stream or no contact can remain, for example if the spikes do not penetrate to the inside of vessel 102 or if the portion which is penetrated is outside the seal. By suitable distortion of the port, a port may be applied from inside a blood vessel and then seal such that most or all of the port is outside the blood vessel.

An eighth issue is the amount of eversion caused by the port. Two measures of eversion can be recognized, the angle between the everted portion and the rest of the vessel and the length of vessel which is everted out of the plane of the vessel surface. In various embodiments described herein, different degrees of both measures may be achieved. In some cases, for example in Aortic hole-closing, it may be desirable to minimize both measures of eversion.

A ninth issue is the profile of the closed hole. The profile depends both on the eversion and on the shape of the port when it is sealed. In some applications, it is desirable that the port be as flush as possible with the vessel surface, lack and sharp edges and/or have a minimum effect on the inner lumen of the blood vessel. In other applications some or all of these features are not required. In some embodiments described herein, the port may be axially compressed or its protruding lips cut off or folded down, to minimize the protrusion of the device from the vessel surface. This further distortions may be passive, active, triggered by the collapsing of the device, and/or meditated by a time delay, such as by the dissolution of bio-absorbable pins holding the port together.

A tenth issue relates to the relative distortion and/or motion of the spikes as compared to the body of the device. In some embodiments, the spikes move independently of the ring, for example bending and/or unfolding. In other embodiments, it is the ring that distorts with a possible result of movement of the spikes. In other embodiments, various combinations of the rings distorting and the spikes distorting may be employed.

The above devices have been described mainly as temporary ports. However, it is noted that when an anastomosis is made, and fails to be completed, the effect is similar to that of a port. In a preferred embodiment of the invention, an anastomosis device is provided that self-seals if the anastomosis is not completed. Various embodiments of anastomosis devices are described in the above referenced PCT application of even date.

Figure 4:
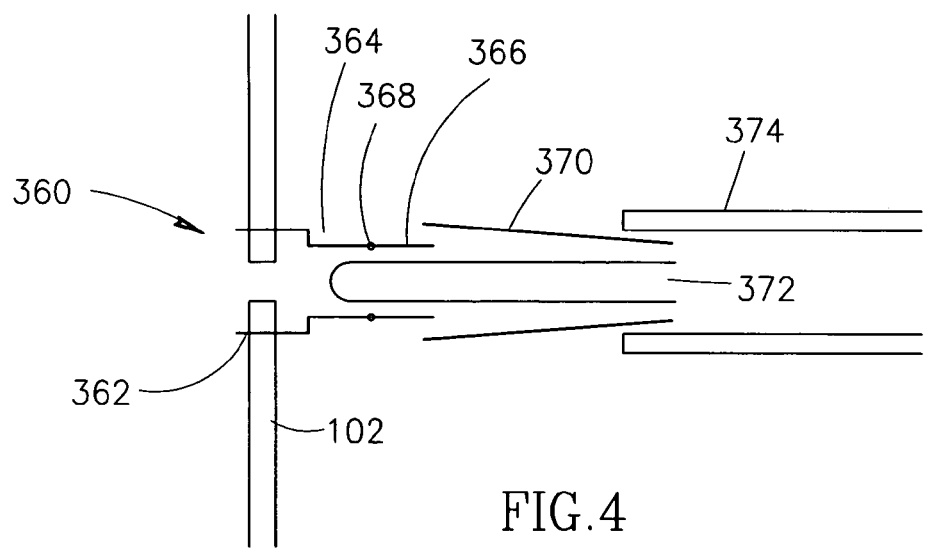
FIG. 4 illustrates an anastomosis connector which selectively seals or completes an anastomosis, in accordance with a preferred embodiment of the invention.

FIG. 4 illustrates a side cross-sectional view of an anastomosis device 360 which can be used to selectively seal itself or complete an anastomosis. Device 360 comprises a plurality of spikes 362 which engage vessel 102 and a cylindrical sleeve, comprising a proximal (to the spikes) portion 364 and a distal portion 366. The two portions are bridged by a pivot 368. In an anastomosis mode of operation, an inner mandrel, such as a catheter 372 is provided in the lumen of port 360, adjacent to proximal portion 364. A blood vessel 374 is brought over distal portion 366 and then the radius of the distal portion is increased to engage the blood vessel. As described in the PCT application filed on even date, this increase in radius can also cause spikes to extend from portion 366 into vessel 374. The increase in radius can be, for example, by inflating a balloon inside the lumen, adjacent portion 366 or by portion 366 being having a resting configuration with a larger radius, which configuration is prevented from being achieved by a restraint, such as an outer tube 370. Once the restraint is removed, the radius of distal portion 366 increases and the anastomosis is completed. The cross-section of proximal portion 364 is preferably not affected because its shape is maintained by catheter 372. Therefor, in a preferred embodiment of the invention, some amount of plastic deformation is achieved at pivot 368.

If an anastomosis in not desired, for example if vessel 374 fails at its other end, vessel 374 is not provided and neither is catheter 372 (at least not to proximal portion 364). Pivot 368 preferably comprises a ring which is restrained from having its radius change. Thus, when the radius of portion 366 is increased, pivot 368 transfers the force to portion 364, whose radius decreases, causing the port to seal, for example by the spike moving towards each other. Preferably, the materiel characteristics of pivot 368, distal portion 366 and proximal portion 364 are selected so that pivot 368 (and not portion 366) will plastically distort under the force of the expansion of portion 366. However, pivot 368 is preferably strong enough to resist plastic deformation at a force which is strong enough to distort the most proximal section of proximal portion 364, so that moving of the spikes is a preferred occurrence to plastic distortion at the pivot.

Figure 5:
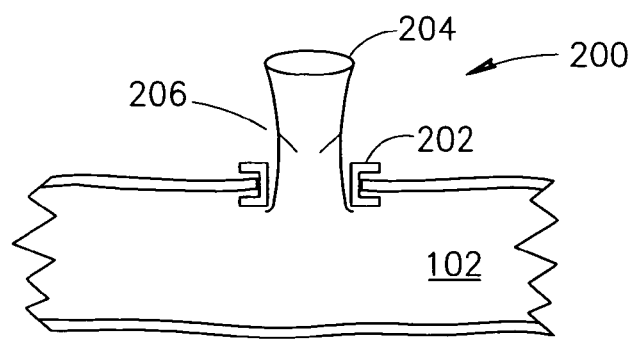
FIG. 5 illustrates a two part port, comprising a sleeve and a sealing portion, in accordance with a preferred embodiment of the invention.

FIG. 5 illustrates a two part port 200, comprising a short sleeve 204 and a sealing portion 202. During operation of the port, a tube (not shown) can be brought into (or out of) blood vessel 102 through sleeve 204. When the usage of port 200 is completed, sleeve 204 is removed and sealing portion 202 is closed (actively, passively or triggered), thus sealing the hole is vessel 102. Optionally, a valve portion 206 is provided, to prevent the loss of blood when there is no tube in vessel 102. Preferably, sealing portion 202 remains in vessel 102 after the procedure is completed.

Figure 6A:
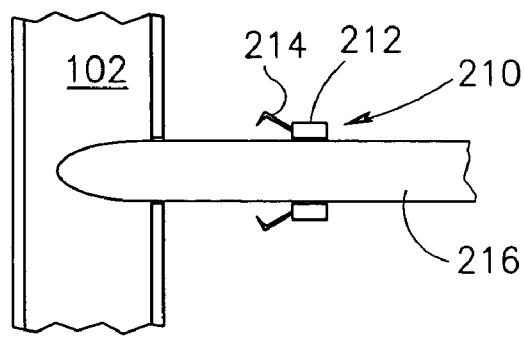
FIG. 6A illustrates a port sealer, which is brought over a catheter or other tool to a hole in a blood vessel and, when deployed, seals the hole.

FIG. 6A illustrates a port sealer 210, which is brought over a catheter or other tool to a hole in a blood vessel and, when deployed, seals the hole. As used herein the term "deployed" means that the device is attached and activated so that it performs at least one of its functions. In the example of FIG. 6, port sealer 210 comprises a ring portion 212 and a plurality of spikes 214. It should be noted that many devices described herein may be used alternatively as ports or as hole closures. In some embodiments, a port may be brought over a catheter to close an existing hole. Generally, the distinction between ports and hole closures is one of specialization: a hole closed can be more easily provided over a catheter and may be more difficult to work through. In addition, devices which include additional functions, such as valves may be limited to only one use. In a preferred embodiment of the invention, sealer 210 is brought over a catheter 216 towards vessel 102. Spikes 214 engage vessel 102. The catheter is preferably retracted at least out of the lumen of the blood vessel. Sealer 210 (or ring 212 thereof)

is then (or at the same time) distorted, bringing spikes 214 towards the center of the hole and sealing the hole (once catheter 216 is removed).

As shown in FIG. 6A, the outer diameter of sealer 210 is substantially greater than that of catheter 216. In a preferred embodiment of the invention, a sealer having a substantially same diameter as the catheter is provided. In one preferred embodiment of the inventions, spikes 214 are formed to desire elastically to touch or cross each other. Spikes 214 are forced apart enough so that they fit over the diameter of catheter 216. Once the spikes engage vessels 102, catheter 216 is removed and the spikes fold in to seal the hole. In another embodiment of the invention, spikes 214 are folded in by an action of inflating a balloon in (or releasing a restraint) on ring 212.

Figure 6B:
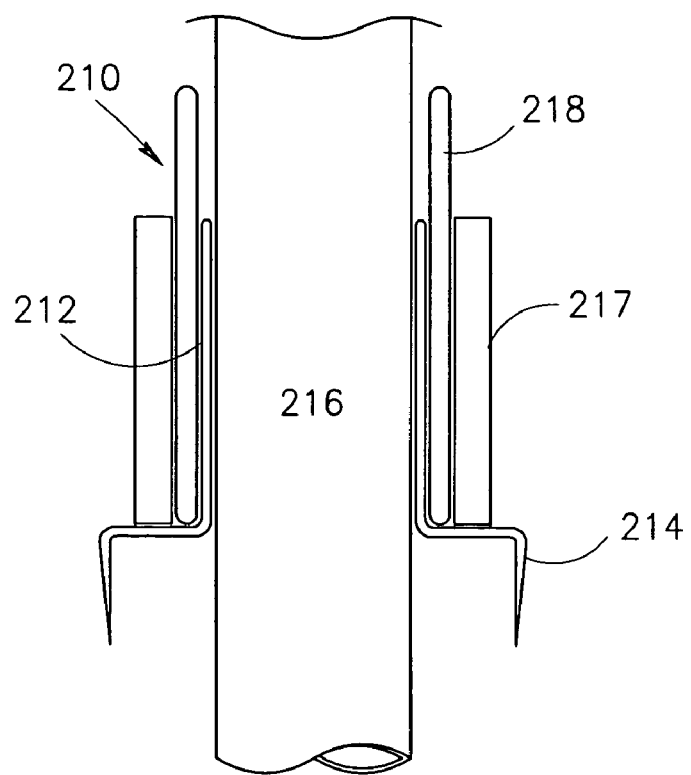
FIGS. 6B and 6C illustrate the deployment of a variant of the device of FIG. 6A.
Figure 6C:
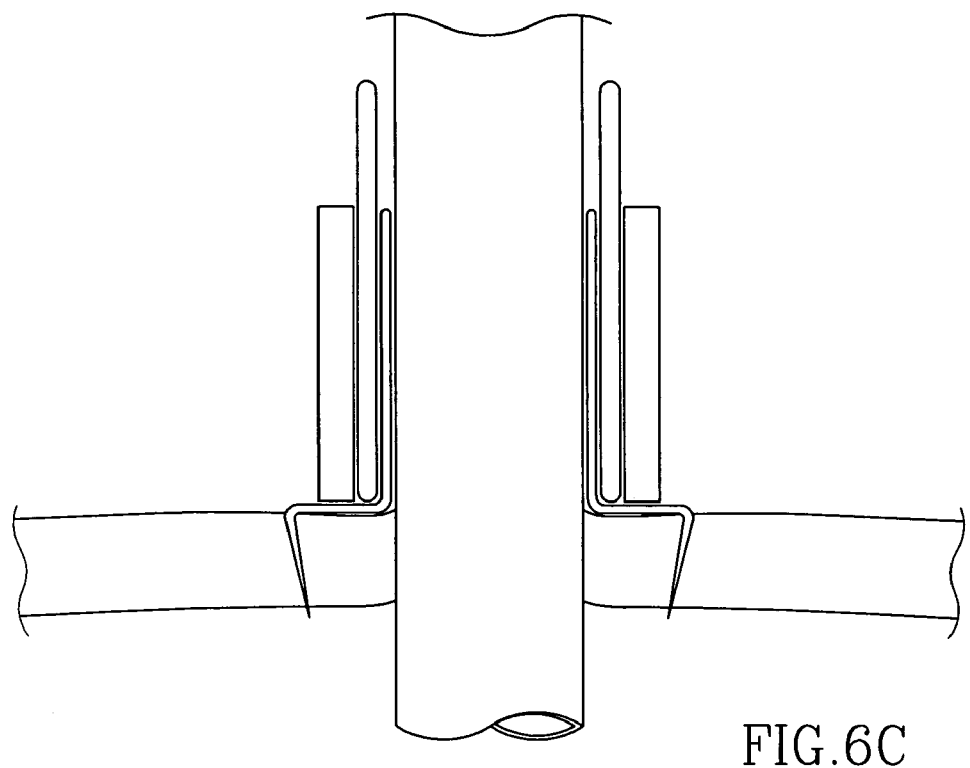

FIG. 6B illustrates a variant of device 210, mounted on catheter 216. In the variant shown, an outer sleeve 217 is provided around ring 212 and an optional balloon 218. In FIG. 6C, device 210 is advanced so that spikes 214 engage the blood vessel. After catheter 216 is removed, device 210 may be collapsed, for example by super-elasticity of the device.

Figure 6D:
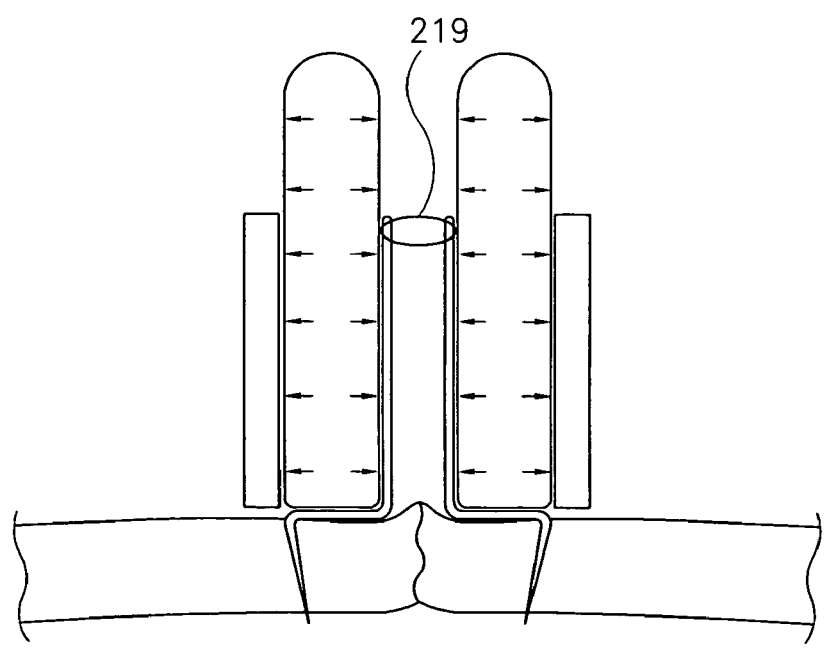
FIG. 6D illustrates sealing a port using a balloon, in accordance with a preferred embodiment of the invention.

FIG. 6D illustrates a method of collapsing using a balloon, in which balloon 218 is inflated against sleeve 217, thereby compressing at least part of ring 212 and causing spikes 214 to move together and seal the hole. In a preferred embodiment of the invention, the part of ring 212 (actually a sleeve) which is further from the blood vessel is made more rigid so that the collapsing of the ring is more pronounced nearer the vessel. Alternatively or additionally, ring 212 may be manufactured to selectively rigid and ductile at different axial locations thereof, preferably so that parts of the ring along the same axial line as spikes will distort more, concentrating the effect on the spikes. Alternatively or additionally, a portion 219 of the ring, preferably at its far end, is made substantially rigid, so that it can act as a pivot for urging the spikes together. As a result, the axial length of ring 210 is preferably reduced. Alternatively or additionally, by allowing different relative radial compression along the ring, balloon 218 better engages device 210 and is less likely to slip off during the inflation.

The embodiment of FIG. 6 is an example where a combination of elastic and plastic distortion may be useful. Elastic (passive) distortion to close the hole to substantially eliminate any blood leaking after catheter 216 is removed, for example by the base of the ring collapsing; and a further sealing of the hole by plastic distortion of more distal portions of the rings, to ensure a complete seal.

With reference to portion 219 it is noted that portion 219 can serve as a pivot (as in FIG. 4) for a different type of lever, one in which the distal (from the spikes) end of device 210 expands and portion 219 pivots the expansion to urge the spikes together. In one example, portion 219 is between the spikes and the end of the ring and a balloon is inflated inside the end of the ring, rather than outside of it. In another example, the end of the ring may be restrained from resuming an expanded position by sleeve 217. Once the sleeve is removed, the distal end of the ring expands and causes the spikes to collapse towards each other.

In some embodiments of the invention, portion 219 (or pivot 368 of FIG. 4) may be provided as a movable element, being part of the port or being provided as an external restraint. Thus, by selectively locating the pivot and the location at which force is applied to the device, various configurational changes may be achieved.

Alternatively or additionally, sealer 210 utilizes a double action mechanism. The sealer is provided at a diameter similar to that of catheter 216. A first activation of the sealer causes spikes 214 to extend outwards, as shown in FIG. 6A. A second activation of the sealer causes the spikes to move towards each other. These activations can be by passive, active and/or triggered distortion mechanisms. As can be appreciated, in some embodiments of the invention, ring 212 is not required to be a complete ring. For example, ring 212 can formed of a plurality of abutting parallelograms.

Figure 7:
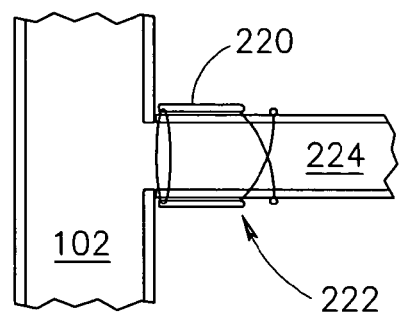
FIG. 7 illustrates a port sealer, in which the sealer cuts off a portion of a blood vessel while performing the seal.

FIG. 7 illustrates a port sealer 220 in which the sealer cuts off a portion of a blood vessel (or graft, electrode, wire or other tube) 224 which is connected to vessel 102. In the example of FIG. 7, an iris cutter 222 pinches, cuts and/or seals vessel 224. Possibly two sets of irises 222 are provided, one to seal and one to cut off. This type of seal (and the one of FIG. 6) is especially suitable for correcting a failed anastomosis. Possibly, the application of pressure using a balloon, as in FIG. 6D, is performed only if necessary (i.e., a leak). Additionally, such a port (or suitable variations of the ports described herein) may be used for vessel ends, for example during certain types of bypass procedures using mammary arteries. In a particular embodiment, iris 222 comprises a plurality of hard leaves which lay flat against the inner surface of the lumen of the port. When an inner restraint is removed, these leaves fold inwards, sealing the enclosed blood vessel and/or severing it. This type of mechanism, as well as others described herein, can also be used to seal an end of a blood vessel, rather than a side thereof.

FIGS. 8A–8B illustrates a hole sealer 230 in which the sealer is not in the same plane of the surface of the blood vessel and in which it is possible to avoid any contact between the sealer and the blood flow. FIG. 8A illustrates sealer 230 in an open configuration, in which vessel 102 is engaged by a plurality of spikes 234. FIG. 8B illustrates sealer 230 in a closed configuration, in which a pressure ring (or members) 232 pinch vessel 102 forming a seal, so that there is no contact between the blood flow and sealer 230.

Figure 8D:
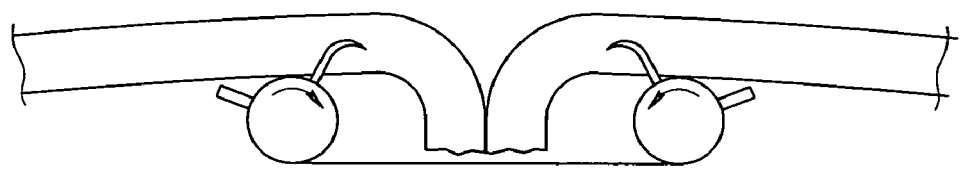

FIGS. 8C and 8D illustrate a port sealing device 350 suitable for closing a hole without any contact with the blood flow. Device 350 comprises a ring 352, preferably a doughnut-shape, but possibly a flat band, having thereon a plurality of spikes 354. One or more protrusions 356 are preferably formed on the ring and are preferably engaged by a holder 358 with a track that preferably matches the protrusions.

When holder 358 is retracted, ring 352 distorts (preferably elastically, super elastically or based on a shape memory) around its median axis, as shown in FIG. 8D, so that spikes 354 engages the vessel and urge it closed. Alternatively or additionally, ring 352 may collapse or otherwise distort so that it has a reduced radius or at least to cause the spikes to move towards each other. A smaller amount of distortion can also achieve a hole closing effect and may be used in some preferred embodiments of the invention.

In a preferred embodiment of the invention, device 350 acts as a fail safe for vascular surgery. If holder 358 is disturbed or otherwise slips off of protrusions 356, the device seals the hole in the blood vessel. the hole can be reopened using a suitable tool which distorts the configuration of FIG. 8D back to the configuration of FIG. 8C. In a preferred embodiment of the invention, a second plurality of spikes 353 is provided which spikes engage the vessel, so that device 350 will stay attached to the vessel rather than to the holder, of the holder moves.

In a preferred embodiment of the invention, a port device is attached to a blood vessel from inside the blood vessel.

Figure 8E:
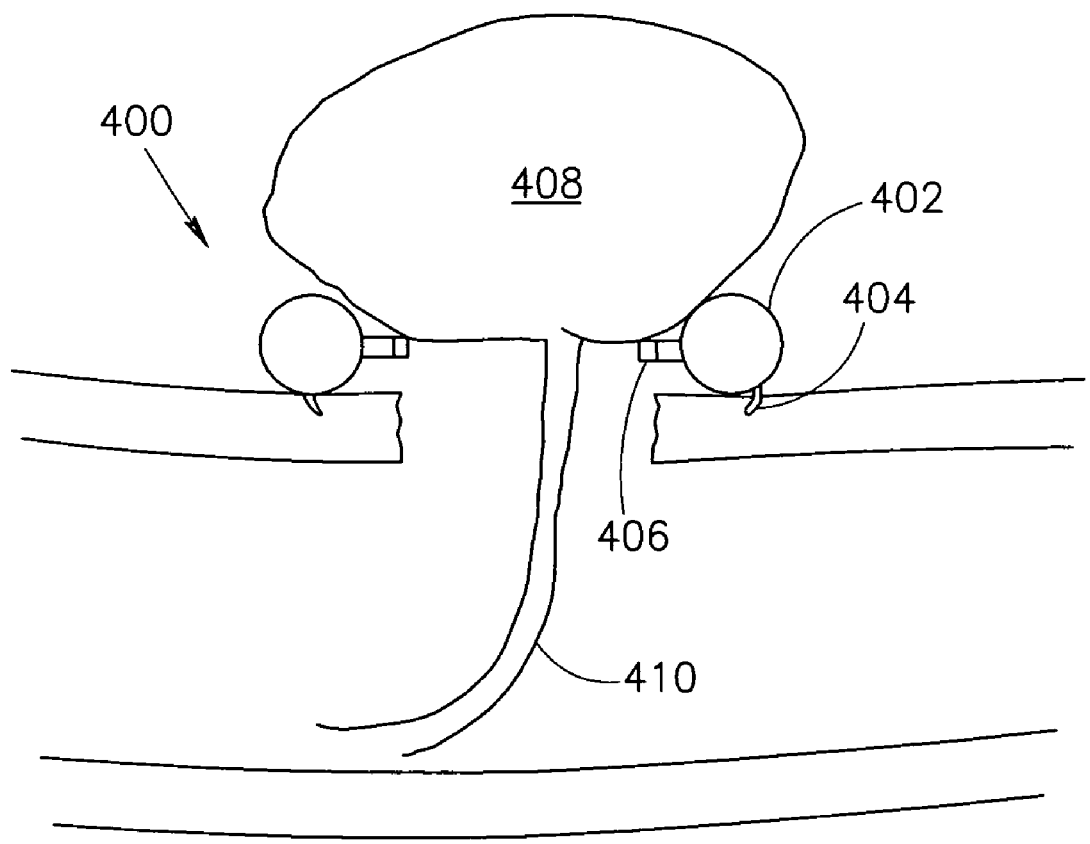
FIG. 8E illustrates a hole sealer which is provided to an outside of a blood vessel from inside of the blood vessel, in accordance with a preferred embodiment of the invention.

For example, if device 350 is super-elastic, it can be radially compressed so that it can be provided through the hole, while maintaining it in the configuration of FIG. 8C, by engaging protrusions 356. FIG. 8E shows such a deployment of a device 400. In a preferred embodiment of the invention, device 400 is pushed out of the blood vessel while being maintained in a compressed configuration, so that it fits through the hole. This can be achieved by providing it through a catheter (not shown). Once the device is outside the blood vessel, a balloon 408 is inflated so that it engages a plurality of protrusions 406 (similar in function to protrusions 356), to prevent the device from closing the hole. Alternatively, a tube may be passed through the lumen of device 400 to provide a working channel and this tube may include indentations, protrusions, an inflatable cuff or other means to engage the protrusions. Balloon 408 can also be used to force device 400 against the blood vessel so that spikes 404 (or other spikes, not shown) engage the blood vessel. when the balloon is deflated, the device distorts and the hole closes. The balloon, in its deflated state is preferably pulled out through the hole.

Figure 9A:
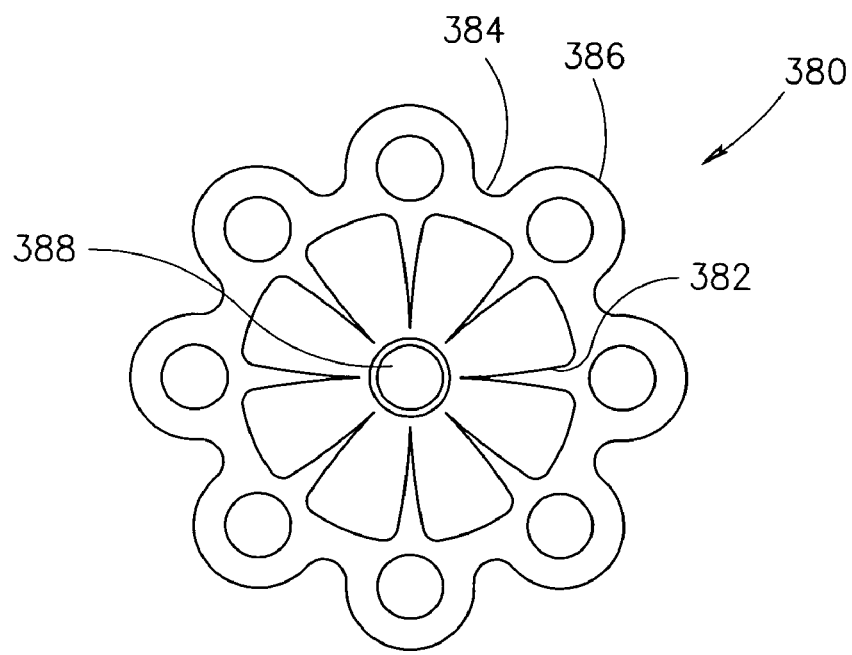
FIG. 9A illustrates a port sealer whose configuration is modified using one or more threads, in accordance with a preferred embodiment of the invention.

FIG. 9A illustrates a port 380, which is distorted using threads. Device 380 has a plurality of spikes 382 arranged on a ring 384. In addition, a plurality of anchors (for threads) 386 are provided, for example holes. During deployment, spikes 382 are bent forward (into the figure plane) to engage a blood vessel. Possibly, this bending is achieved by folding the anchors 386 up out of the figure plane. This distortion may be plastic or elastic. A loop of thread is preferably threaded through each one of anchors 386. When sealing the port, the loops are all pulled towards the center of the device, for example if the other side of the loop is threaded through a ring 388 (not part of the port). Thus, the port collapses and becomes sealed.

Figure 9B:
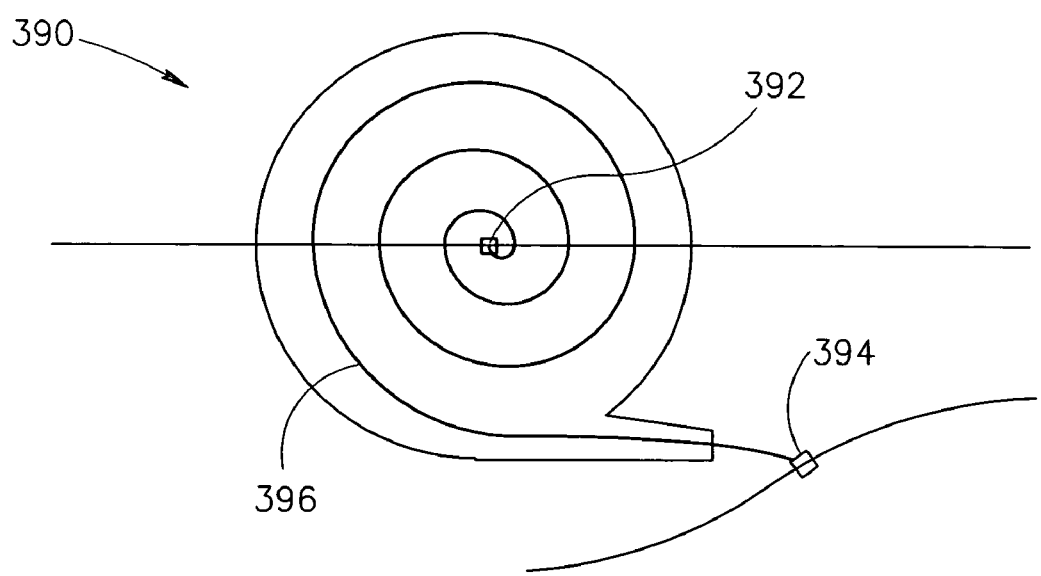
FIG. 9B schematically illustrates a thread retractor, in accordance with a preferred embodiment of the invention.

FIG. 9B schematically illustrates a thread retractor 390, in accordance with a preferred embodiment of the invention. A first thread from a purse string stitch is attached to an anchor 392. A second thread is attached to an anchor 394, which is at the end of a retractor 396, for example a spiral spring as shown. When the purse-string stitch is performed, device 390 is preferably connected to the ends of the threads, either near the stitch, for example inside the body or further away, such as outside the body. Thus, various sizes of device 390 may be used. If a tube is inadvertently removed from the purse string, retractor 396 is able to pull the thread and close the hole, preventing sever blood loss. Preferably, the tension in the retractor is selected to be large enough to pull the purse-string closed but not so large that it damages the vessel at the points where the thread is connected. Preferably, anchor 392 and/or anchor 394 is a ratchet anchor, which allow the movement of thread only in one direction, so that threading the anchors is easier.

The above description has focused on temporary ports and anastomosis devices. However, it should be noted that the same or similar devices can be used for sealing holes and/or making other repairs in blood vessels. Such a sealer can be provided over a catheter which is inserted into a hole. The catheter preferably comprises inflatable cuffs which can be used to block blood flow from the damaged area while the sealing is being performed.

Additionally, the above devices can be used for inserting a small diameter wire or tube into and/or out of a blood vessel. Typically, a relatively large diameter catheter is required for guiding the wire to its destination. In some cases, the wire may have a larger tip, for example a sensor or a pacing electrode. In a preferred embodiment of the invention, the wire and catheter are provided through a port as described herein. When the catheter is retracted the port is sealed, on the wire. Preferably, the seal is also utilized to stabilize the position and/or rotation of the wire.

A different use for passing a wire through a seal of the port is to ease the reopening of the port. As indicated above, some types of ports can be opened after they are sealed. In a preferred embodiment of the invention, the wire is coupled to the port. When it is desired to open the port, a catheter is guided over the wire to the port. Preferably, a greater contra-force on the port can be generated by pulling on the wire while advancing the catheter. Thus, there is also less danger of applying force against a part of vessel 102 opposite the port. If the wire passes through the seal, in a preferred embodiment of the invention, the catheter is advanced along the wire until it passes through the port. Alternatively or additionally, pulling on the wire distorts the port so that it opens, is easier to open or is able to be opened, from the force of the catheter against it. In some embodiments, the wire is attached to the portion of the port which is outside the blood vessel.

FIGS. 10A–10E illustrate an aortic hole closure device 500 having a flat profile and deployment thereof, in accordance with a preferred embodiment of the invention. A similar device may also be used for other vascular structures.

Figure 10A:
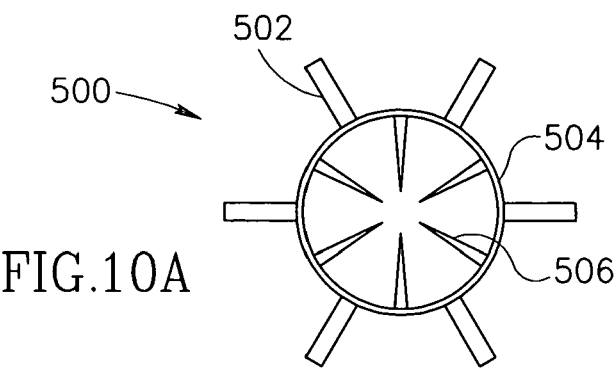
FIGS. 10A–10E illustrate an aortic hole closure device having a flat profile and deployment thereof, in accordance with a preferred embodiment of the invention.

FIG. 10A shows device 500 in a top view in its relaxed state, showing a plurality of inward pointing spikes 506 and a plurality of holding tabs 502, interconnected by a ring 504. Although six spikes and tabs are shown, a different number of spikes and/or tabs may be used. additionally, the spike sand tabs are shown staggered, however, they may be aligned. Alternatively to a circular ring, a ring of other geometric shapes, such as an ellipse, a triangle or other polygons, may be used.

Device 500 is designed so that when the tabs are held perpendicular to the plane of ring 504, the ring distorts and the spikes point downwards. When the tabs are released, the tabs flatten out to substantially the plane of the ring. In some embodiments of the invention, one or more inward pointing tabs (in the plane of ring 504, in a relaxed state, not shown) are provided, for example for guiding the tissue engaged by device 500 to a desired configuration. In a preferred embodiment of the invention, device 500 is deforms elastically or super-elastically or is formed of a shape-memory material.

Spikes 506 are preferably curved. Alternatively or additionally, they may be barbed or roughened, to prevent inadvertent retraction. However, the spikes may also be straight and/or smooth.

Figure 10B:
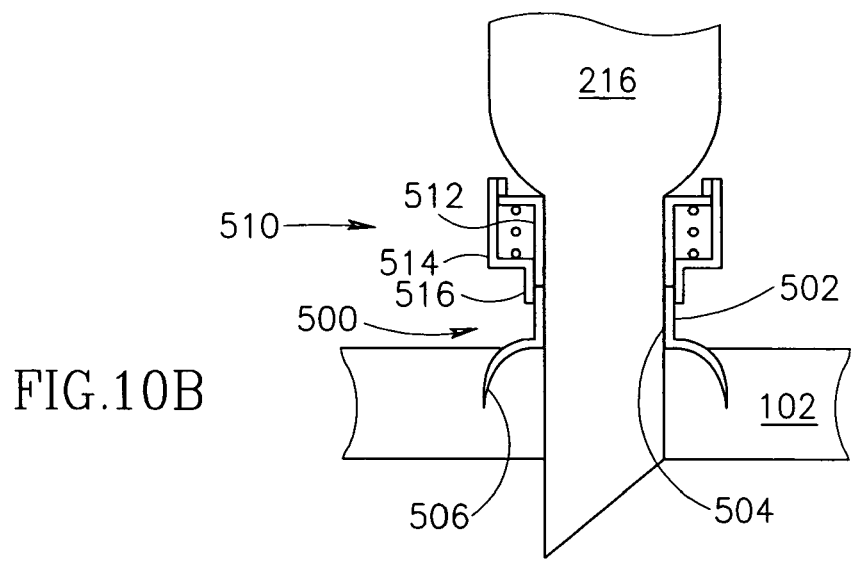

FIG. 10B is a side cut-through view of device 500, mounted on an aortic cannula 216, using a holder 510. In a preferred embodiment of the invention, cannula 216 is sold with holder 510 and device 500 mounted thereon. Alternatively, they may be sold separately. As shown in FIG. 10B, when cannula 216 is inserted into an aorta 102, spikes 506 are forced into the aorta. Preferably, holder 510 is prevented from retracting by a thickening of cannula 216.

Holder 510 preferably comprises an outer tube 514 having lips 516 which hold tabs 502 and an inner tube 512, engaging the cannula. However, other suitable mechanisms, for example replacing tubes with elongate elements will suggested to a person skilled in the art.

As shown, spikes 506 preferably do not penetrate to the inner side of the aorta, however, in an alternative embodiment, at least some of the spikes may be long enough so that they so penetrate.

Figure 10C:
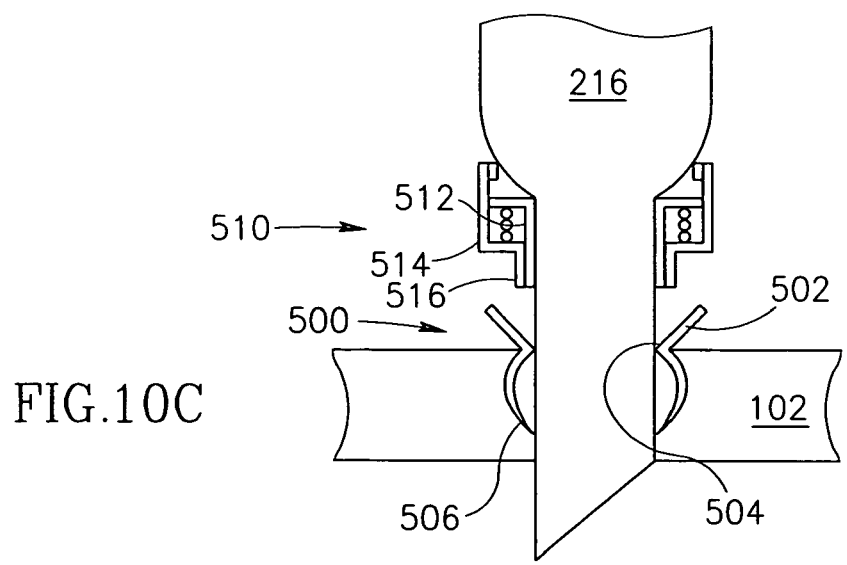

In FIG. 10C, tube 514 (and thus lips 516) are retracted, while tabs 502 are prevented from retraction by tube 512.

However, the retraction of lips 516 release tabs 502 to rotate so that device 500 attempts to return to its relaxed state. However, as shown in FIG. 10C, spikes 506 are stopped from completing their inward motion by cannula 216 and thus also tabs 502 do not complete their motion. At this point, device 500 is better engaged by aorta 102 than by cannula 216, so if cannula 216 is accidentally retracted, device 500 will seal the aorta from leaking.

Figure 10D:
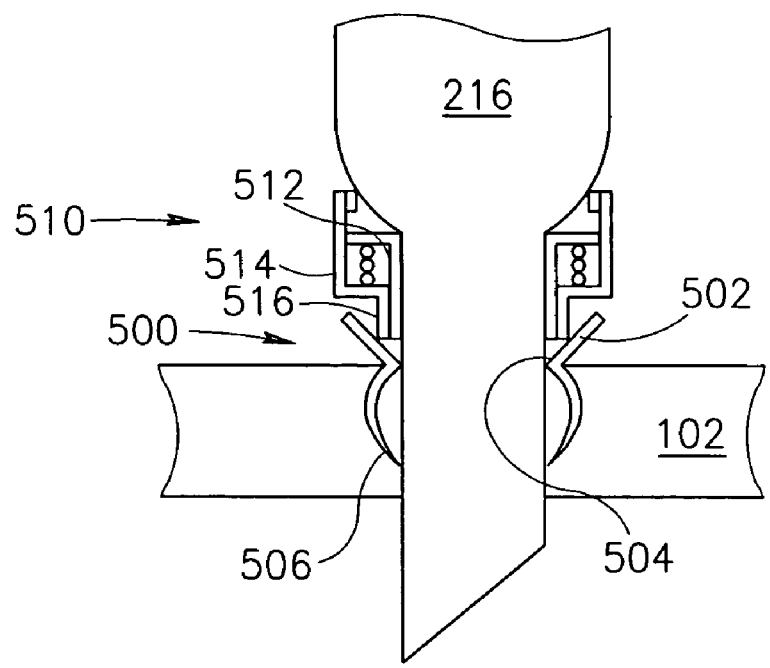

Optionally, as shown in FIG. 10D, tube 514 and lips 516 are advanced again, for example, to assists in keeping device 500 in place and/or to advance it towards aorta 102.

Figure 10E:
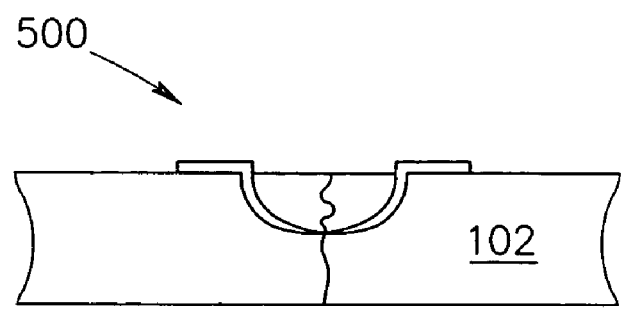

FIG. 10E shows the effect of removing cannula 216, which allows spikes 506 to complete their motion, sealing the hole in the aorta. Preferably, tabs 502 are flush with the surface of aorta 102, so there are no bumps. It is noted that by suitably selecting the length and curvature of spikes 506, aorta 102 can be prevented by protruding out or in, as in some of the previous embodiments. Conversely, also in those embodiments, the sealing of the hole in the blood vessel can result in a final configuration in which all the vascular tissue and/or the connector parts remain in the plane of the blood vessel and do not protrude outwards and/or inwards from the vessel surface. In some cases, the resistance of the aorta is taken into account, such that tabs 502 are not in the plane of ring 504 but slightly below. Thus, even if spikes 506 do not complete their motion, the tabs, or at least their ends, do not stick out.

It should be noted that by maintaining the closed hole in the plane of the vessel wall, it is easier to match up layers of the blood vessel, to promote healing. For example, inner, outer and/or middle layers of the blood vessel are automatically aligned.

Although ring 504 is shown as smooth, alternatively, ring 504 may be undulating, for example in the form of a sine wave. Thus, ring 504 can contact radially during deployment, if desired. Also, this provides some additionally flexibility for the seal.

FIGS. 11A–11E illustrate a femoral hole closure device 520 and deployment thereof, in accordance with a preferred embodiment of the invention. Device can be made similar to that of device 500, however, in a preferred embodiment of the invention, the device is adapted for oblique insertion, for example, the spikes being oblique and the ring being elliptical. Also, as will be explained below, fewer spikes may be used.

FIG. 11A is a top cut-through view showing device 520 mounted on a cannula 216. Device 520 comprises a ring 524, a plurality of spikes 522 and a plurality of tabs 526. In the embodiment shown, the ring is maintained in an ellipse, however, in a relaxed state, the ellipse is preferably narrower than shown in the Fig., to assist in compressing sides of the incision against each other.

In device 520, two opposing spikes are shown. In an alternative embodiment there is one spike on one side and two spikes on the opposite side of the ring. Preferably, the aortic device 500 of FIG. 10 is used to seal a hole in a manner that emulates a purse string suture. Device 520, on the other hand, preferably emulates sealing a linear cut by holding the cut ends together. Thus, fewer spikes may be used, and a distortion of the connector is useful. Also in FIG. 10, the connector may distort in some embodiments. Preferably in FIG. 10, ring 504 distorts (when released) so that it has a smaller radius, for example being formed of a coil or a wave-shape. Alternatively, the ring may distort to have a long radius aligned with the direction of the cut in the aorta and/or at a desired angle relative to the aorta axis. Preferably, guiding notch or groove is provided in the delivery system, to assist in aligning the connector orientation. An aorta-type connector may also be useful where the hole in the vessel is punched out or a "Y" shaped hole, and not a linear incision.

FIG. 11B is a side cut-through view showing device 520 mounted on a femoral cannula 216, prior to penetration into a femoral artery 102. A delivery system 510, similar to that of FIG. 10 is also shown. However, if the fail-safe action of the device is not required a simple over tube for holding back tabs 526 and urging spikes 522 of device may be used instead.

FIG. 11C shows device 520 inserted into the wall of vessel 102.

Figure 11D:
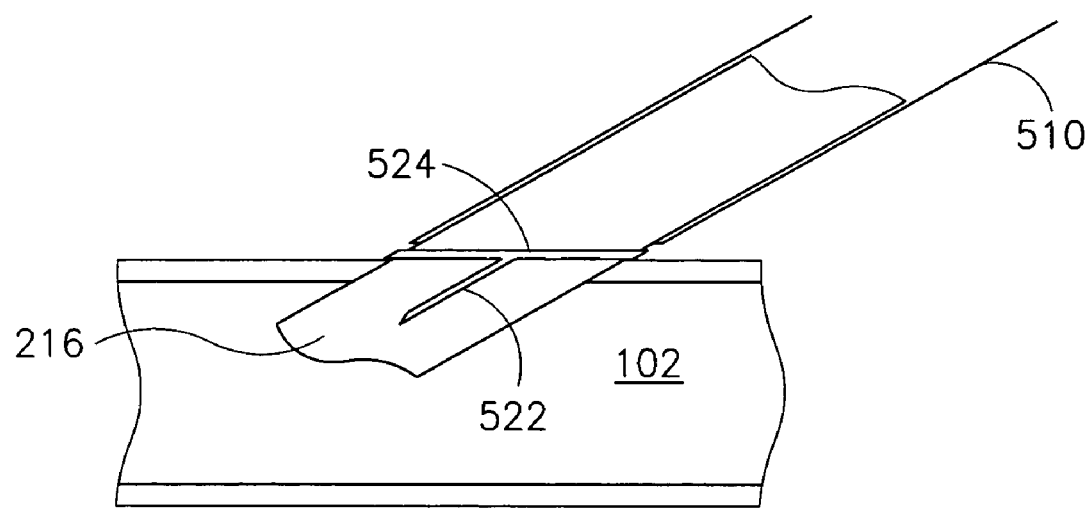

FIG. 11D is a side view of FIG. 11C, showing the oblique angle of spikes 522 in this embodiment. The angle of the spikes is preferably the same as that of cannula 216 relative to vessel 102. Alternatively, the angle may be greater or smaller. Possibly, the spikes and/or the tabs are perpendicular to the ring and not oblique.

Figure 11E:
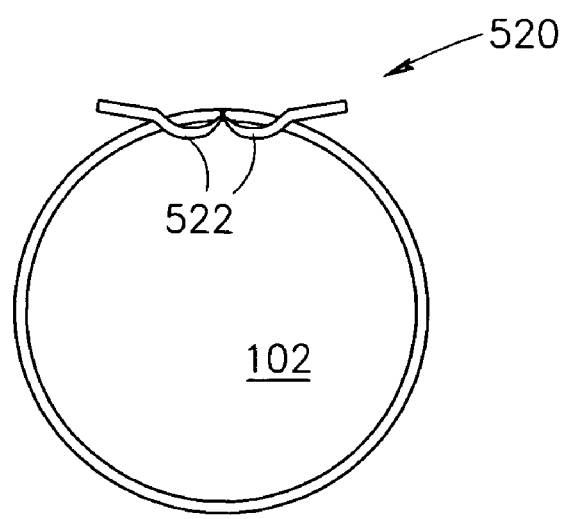

FIG. 11E shows a sealed hole when cannula 216 is removed. The tabs may protrude as shown. Alternatively, the tabs for the side of the artery are formed to conform with the expected shape of the artery after the hole is sealed. Thus, in devices including a plurality of tabs, the tabs may not all be in a same plane. Alternatively, the sealed area is flatter and/or dimpled in from the surface of the artery, so the tabs do not stick out as shown.

Similar to device 500, device 520 is preferably provided in kit form, preferably pre-mounted on cannula 216 of on a port device used to pierce and access vessel 102. In embodiments described below, a hole closure device is provided through cannula 216, and is preferably provided pre-mounted on a suitable delivery system as part of the same or a different kit.

FIGS. 12A–12F illustrate a two part hole closure device 530 and a process of deployment thereof, in accordance with a preferred embodiment of the invention. In a preferred embodiment of the invention, device 530 comprises two parts, an outside base part 532 and an inside spike part 534. Spike part 534 is preferably provided from inside the vessel, while base part 532 is provided from outside the blood vessel, however, their positions and/or functions may be reversed with the receptacles being inside the vessel and the spikes coming from outside. Spike part 534 preferably comprises a base 536 and a plurality of spikes 538. Spikes 538 preferably flare out and are curved, rather than straight. Base part 532 preferably comprises a skeleton, for example a ring 540 and a plurality of receptacles 542 for spikes 538. Preferably the receptacles define circular apertures, however other shaped apertures may be provided instead. Alternatively, receptacles 542 may comprise a thin material punched through by spikes 538. Also a same number of spikes and receptacles is shown, In a preferred embodiment of the invention, a larger number of receptacles, for example surrounding skeleton 540 completely, is provided. A plurality of radial layers of receptacles may also be provided.

Figure 12A:
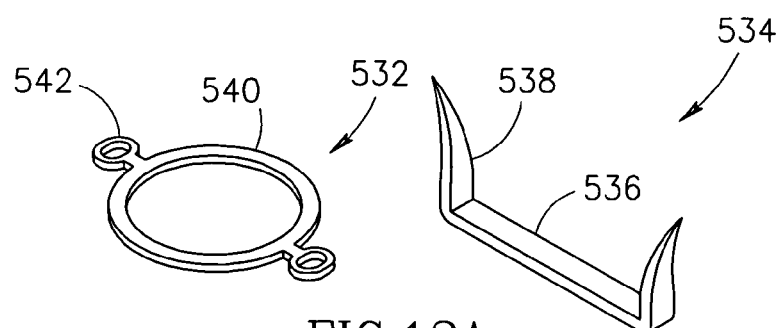
FIGS. 12A–12F illustrate a two part hole closure device and deployment thereof, in accordance with a preferred embodiment of the invention.
Figure 12B:
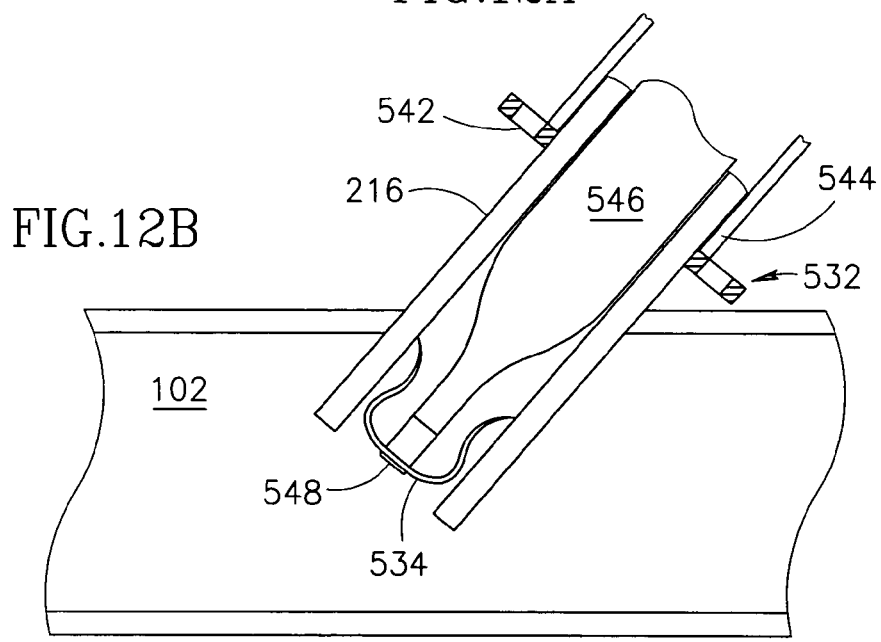

As shown in FIG. 12B, spike part 534 is provided by a spike holder 546 that holds spike part 534 at a tip 548 of the holder, for example spike part 534 placed through an aperture 549 of tip 548. Spike holder 546 is provided through cannula 216. Base part 532 is preferably mounted on the outside of cannula 216 and is maintained in place by a base-holder 544. In these figures a flat connector is shown, which may be used also for sealing oblique port-holes However, alternatively, an oblique connector, for example having an oblique base part, may be used.

Figure 12C:
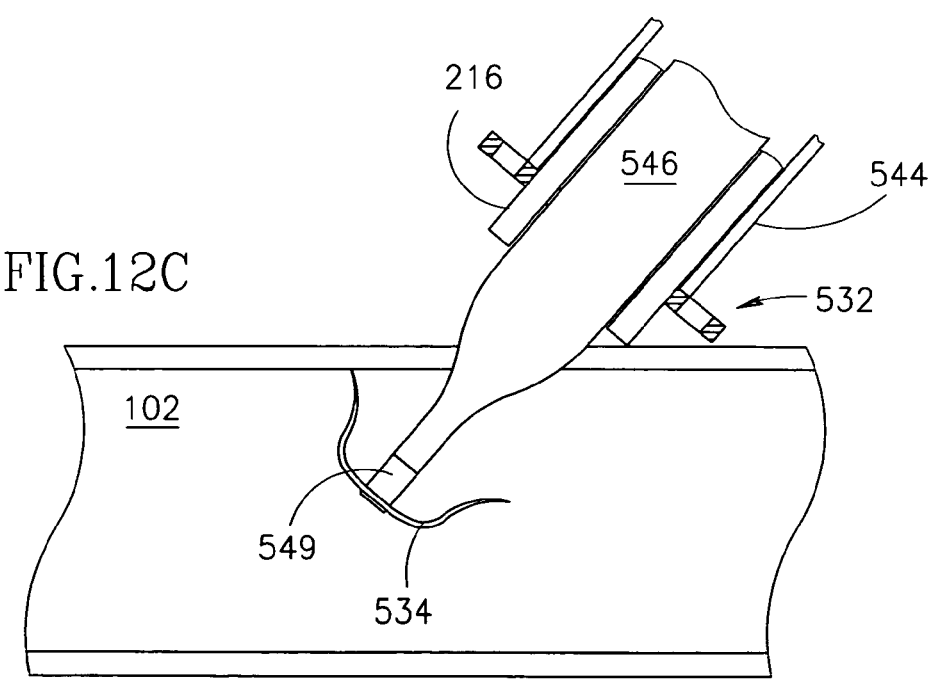

In FIG. 12C, cannula 216 is retracted, so that spikes 536 are no longer constrained by cannula 216 (if they were before) and the hole in vessel 102 closes over spike holder 546.

Figure 12D:
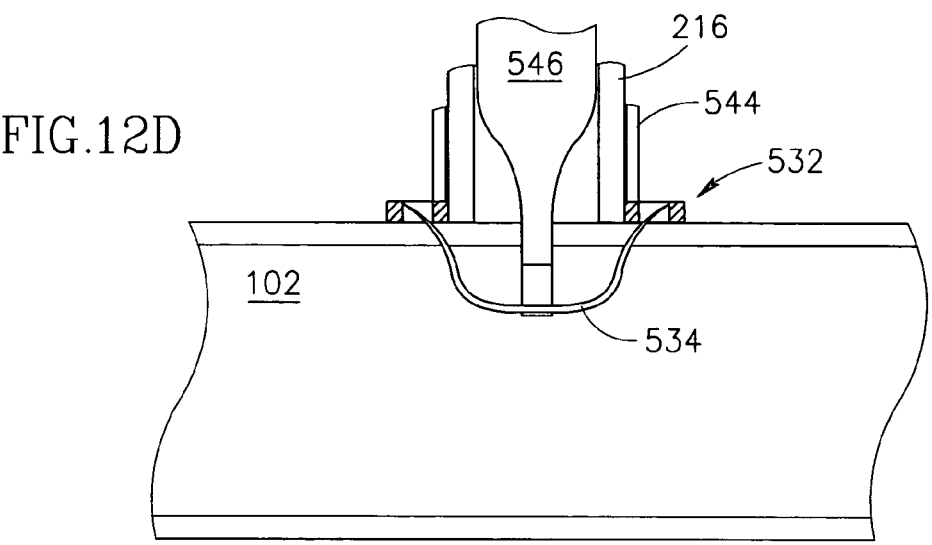

In FIG. 12D, base holder 544 is advanced and spike holder 546 is retracted, such that base part 532 is flat with vessel 102 and spikes 538 are retracted sufficiently to pierce vessel 102, into receptacles 542. Preferably, the end of holder 546 is narrow, so that the hole in the blood vessel is not stretched by holder 546. Stretching by holder 546 may cause spikes 538 to transfix an incorrect part of vessel 102.

Figure 12E:
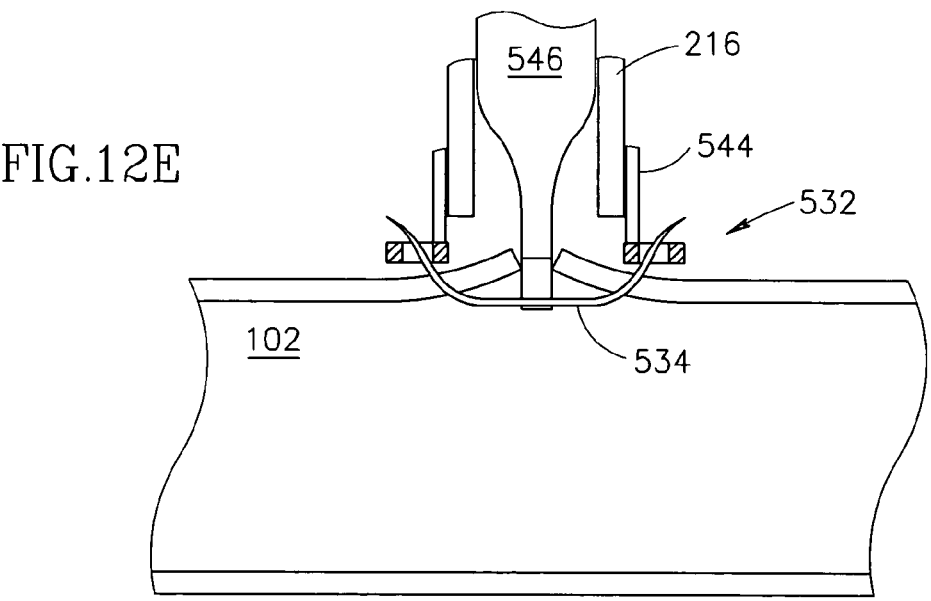

In FIG. 12E, holder 546 is further retracted, further advancing spikes 538 into receptacles 542.

Figure 12F:
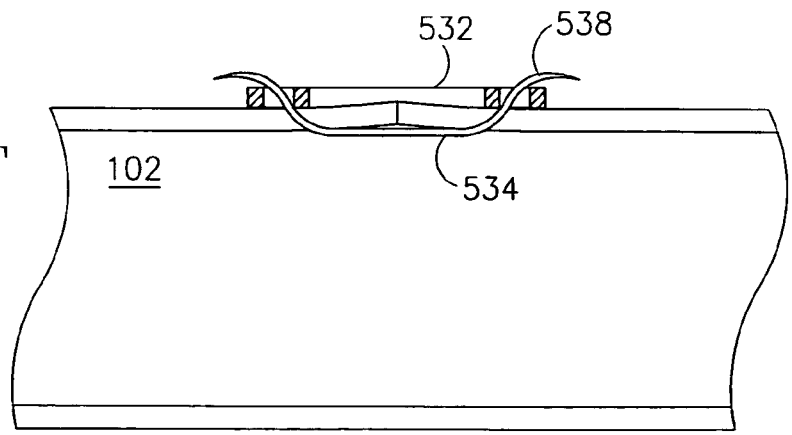

In FIG. 12F, holder 546 releases spike part 534 and exists vessel 102, thereby completing the sealing operation.

In a preferred embodiment of the invention, a determination is made that spike part 534 is inside the blood vessel, prior to retracting cannula 216 (FIG. 12C). In a preferred embodiment of the invention, this determination is made by comparing length markings on an extension of holder 546 and of cannula 216.

Alternatively, holder 546 includes a thin tube (not shown) or an extra thin tube coupled to it is provided, which thin tube fills with blood when its tip is in vessel 102. Cannula 216 may be a multiple-lumen cannula (or a multi-lumen port, catheter or endoscope may be provided), in one lumen holder 546 is inserted and in another lumen a test tube for detecting the blood is inserted.

The mechanism for releasing spike portion 534 from tip 548 of holder 546 may be of many kinds. In one example, tip 548 comprises slot which can hold spike part 534 and even force it through base part 532, but cannot hold it against sufficient force applied by base holder 544. In another example, tip 548 comprises a grasping jaw which can be opened or closed. Possibly, tip 548 comprises a hook having a locking element which completes the hook into a complete enclosure, Thus, little force is applied against the locking element. In another example, holder 546 is screwed onto spike part 534, using a suitable thread on tip 548 and/or base 536.

In an alternative embodiment for tip 548 holding spike part 534, tip 548 includes a slot perpendicular to the axis of holder 546 and two lumens or grooves along the axis of the holder, base 536 is fit into the slot and a wire or suture is provided from outside the body, through one lumen, across the slot and into the other lumen. Alternatively, at least one side of the wire is attached inside holder 546.

As long as both sides of the wire are held, spike part 534 will not move. Once one side of the wire is released, the entire wire can be retracted and spike part 534 can slip out.

Optionally, a small ring or other aperture enclosing structure is provided in the closure device (or in other devices for vascular systems, such as stents or anastomosis connectors) and the wire is threaded through the aperture. Thus, loss of the device can be prevented. In any case, even if such a thread is provided, the device remains a suture-less device, as it does not hold the vessel walls together using a suture.

FIGS. 13A–13E illustrate a one part hole closure device 550 and a process of deployment from inside a blood vessel, in accordance with a preferred embodiment of the invention. In addition, this embodiment shows that a wire holding mechanism as described above can be used to deform a super-elastic connector it is holding in place.

Figure 13A:
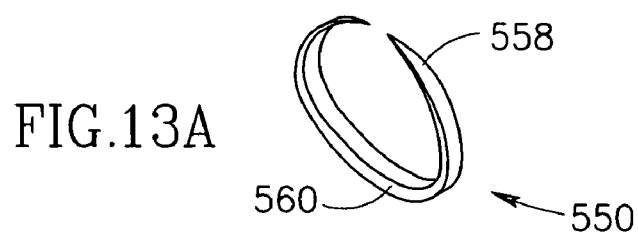
FIGS. 13A–13E illustrate a one part hole closure device and deployment thereof from inside a blood vessel, in accordance with a preferred embodiment of the invention.

FIG. 13A illustrates device 550 in a relaxed configuration. Preferably, device 550 is super-elastic and has a base 560 and arms 558 ending in sharp tips. In an exemplary embodiment, device 550 is a slotted circle. Alternatively, other geometries, such as used for staples and clips in the art may be used. When deployed, device 500 may reach its resting configuration (relaxing), or vessel 102 may prevent its completing the relaxation process, thereby providing some tension in the seal.

Figure 13B:
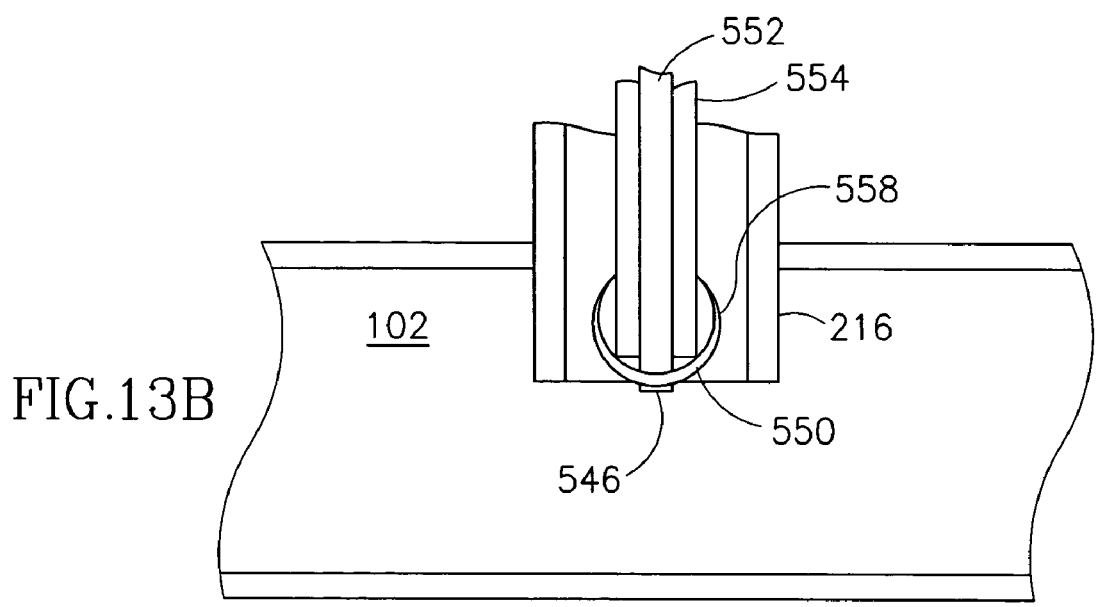

FIG. 13B illustrates a holder 552 which holds device 550 at its tip 556, inside a cannula 216. Many mechanisms can be used to hold device 550 in place, for example as described above. An over-tube/pusher 554 is preferably provided over holder 552 and between the tips of arms 558 and holder 552.

Figure 13C:
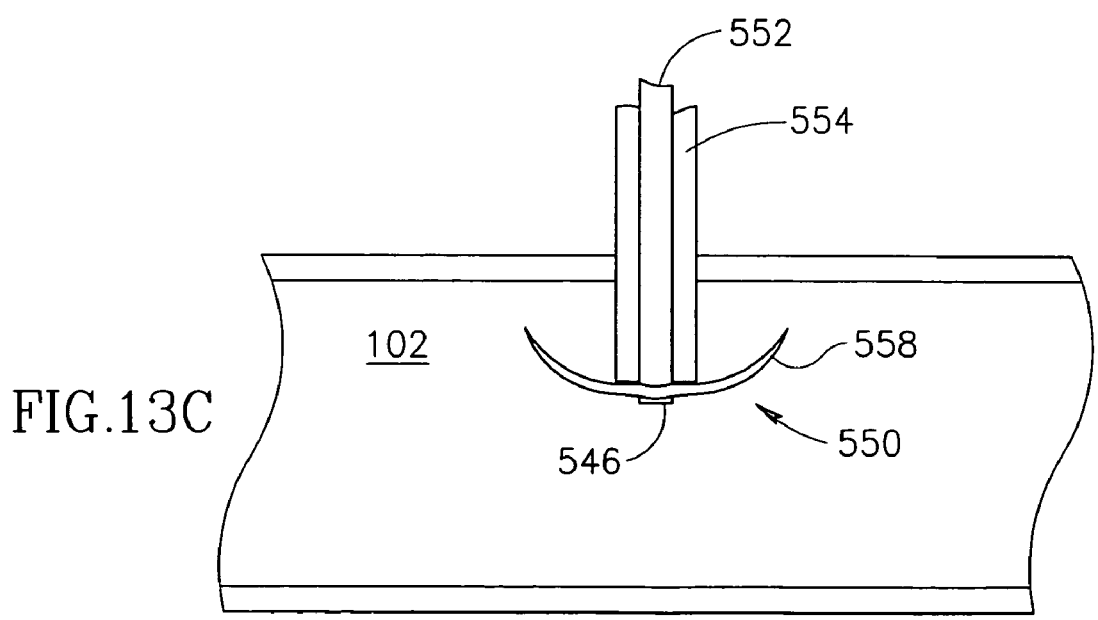

In FIG. 13C, Cannula 216 is retracted and pusher 554 is advanced, so that it spreads apart arms 558 of device 550. Optionally, pusher 554 has slots defined at its end face, to receive arms 558, to prevent torsion.

Figure 13D:
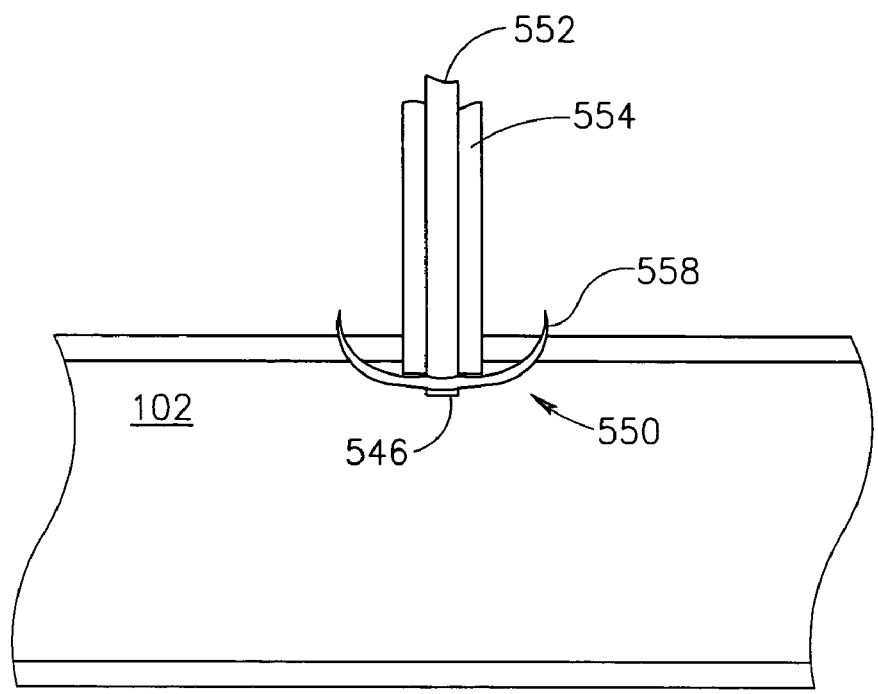

In FIG. 13D holder 552 is retracted so that arms 558 pierces through the walls of the blood vessel.

Figure 13E:
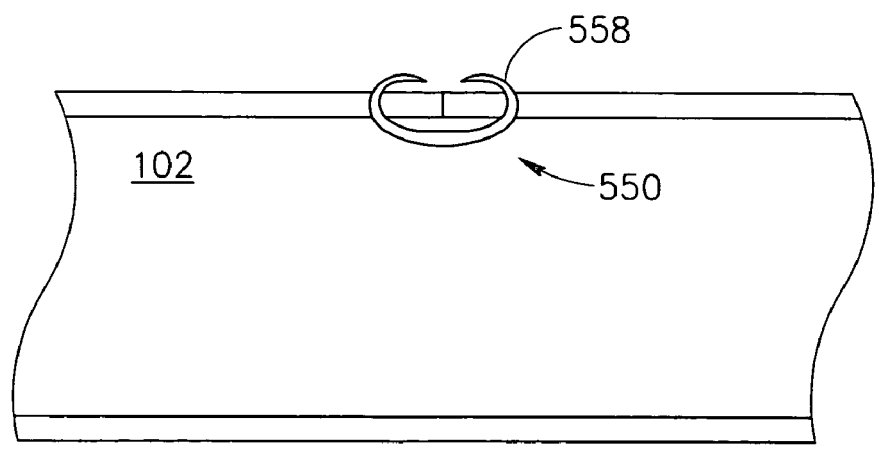

In FIG. 13E, holder 552 is removed and arms 558 return to their relaxed position, sealing the hole.

Figure 14A:
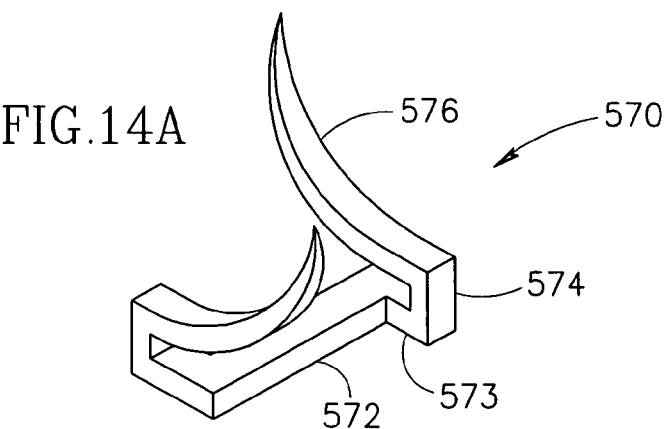
FIGS. 14A–14C illustrate a hole close device and a delivery system for the device in accordance with a preferred embodiment of the invention.
Figure 14B:
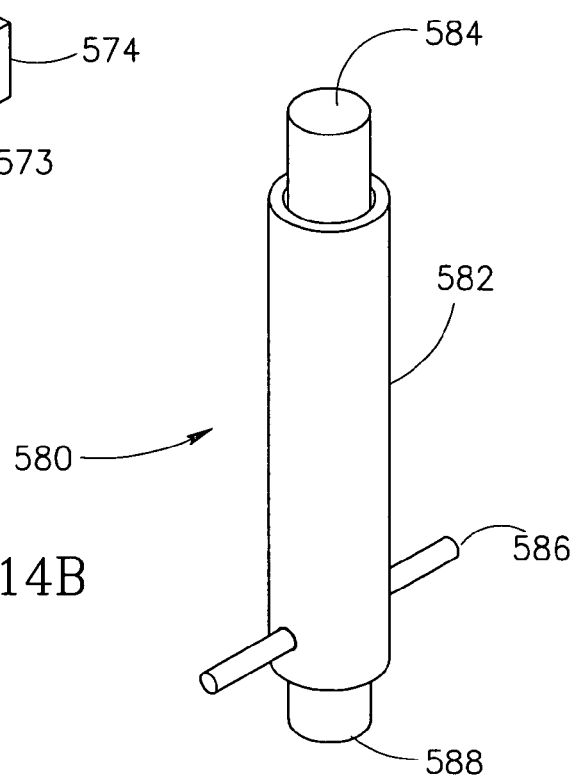
Figure 14C:
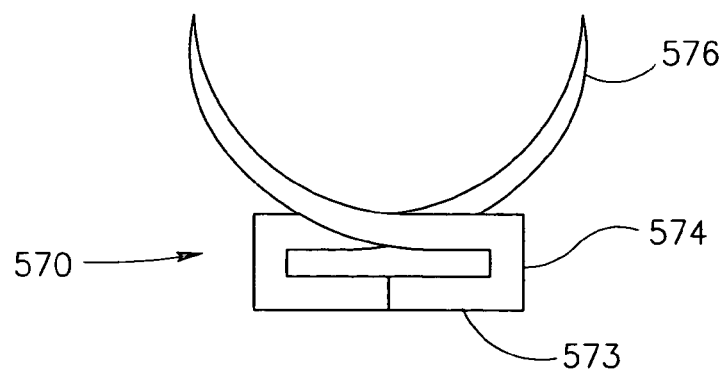

FIGS. 14A–14C illustrate a hole close device 570 and a delivery system 580 for device 570 in accordance with a preferred embodiment of the invention. Device 570 is preferably plastically deformed, as will be described below.

FIG. 14A is a perspective view of device 570, showing a base 572 having two levers 573 extending therefrom. On each lever 573, an extension 574 is provided and a curved spike 576 is mounted at the end of the extension. Although only two spikes are shown, a greater number of spikes may be provided in an alternative embodiment of the invention.

FIG. 14B illustrates a delivery system 580 comprising an inner rod 584 having an end 588 and an outer tube 582 having a pair of pegs 586 extending perpendicular thereto.

FIG. 14C is a view A of device 570, which view will be used in the deployment description, below.

FIGS. 15A–15G illustrate a method of deploying the hole closer of FIGS. 14A–14C.

Figure 15A:
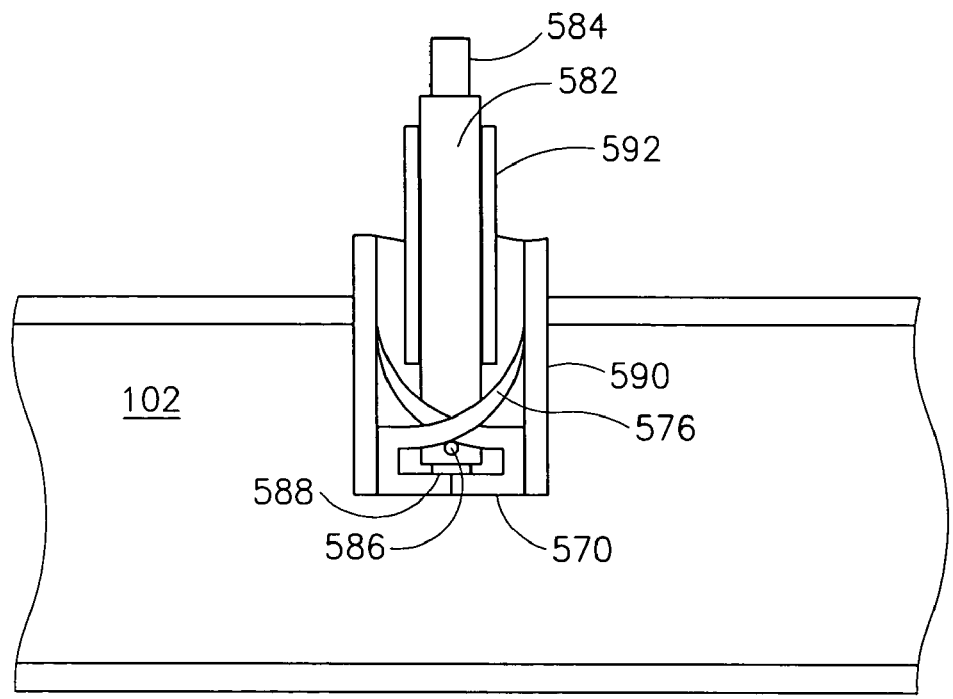
FIGS. 15A–15G illustrate a method of deploying the hole closer of FIGS. 14A–14C.

FIG. 15A illustrates device 570 held between tip 588 of rod 584 and pegs 586. Optionally, tip 588 has a slot formed therein to prevent rotation of device 570. Optionally, tip 588 holds the device using methods as described for FIGS. 12 and 13 above. A pusher 592 is provided over tube 582.

Vessel 102 is protected from spikes 576 by an over tube 590, which may be cannula 216.

Figure 15B:
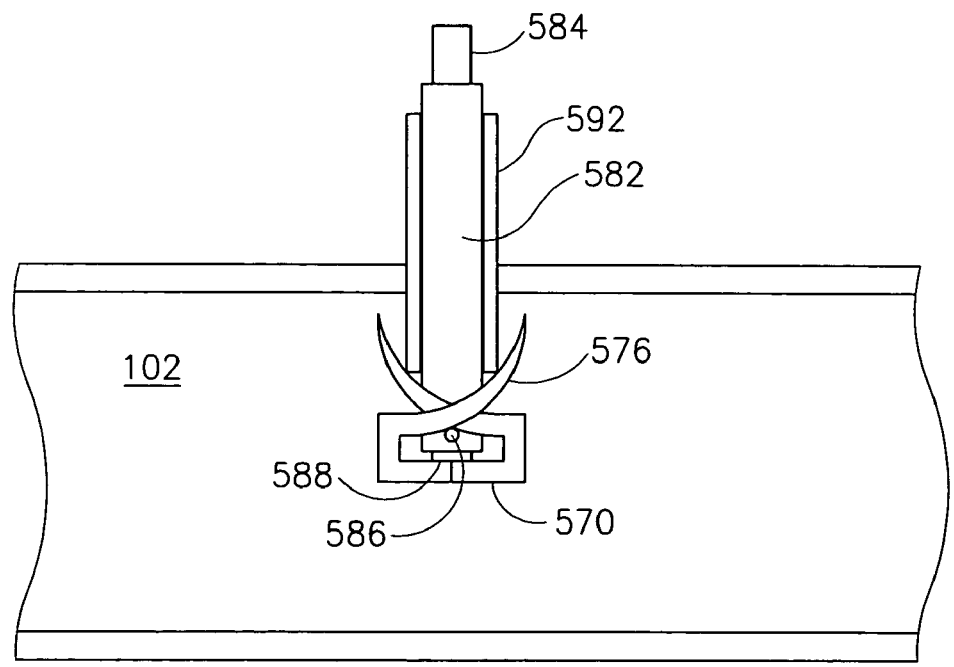

In FIG. 15B, over tube 590 is removed, thereby causing the walls of vessel 102 to close on outer tube 582.

Figure 15C:
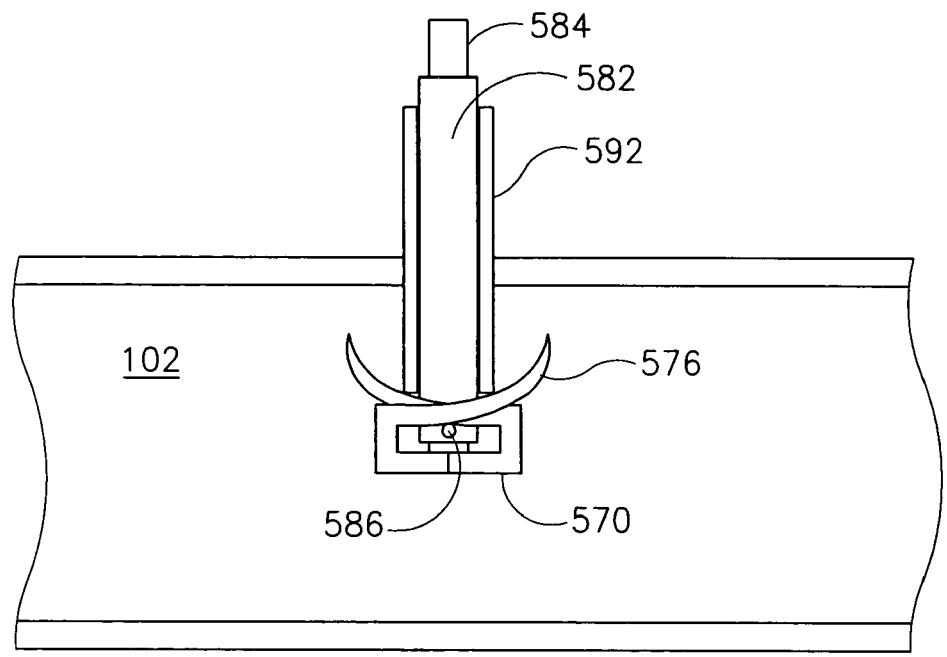

In FIG. 15C, pusher 592 is advanced, causing spikes 576 to bend out. In one embodiment, pegs 586 move with the outer tube, and a counter force is provided by tip 588. Alternatively, the pegs are coupled to rod 584 and not to forward motion of outer tube 582 and they provide the counter force.

Figure 15D:
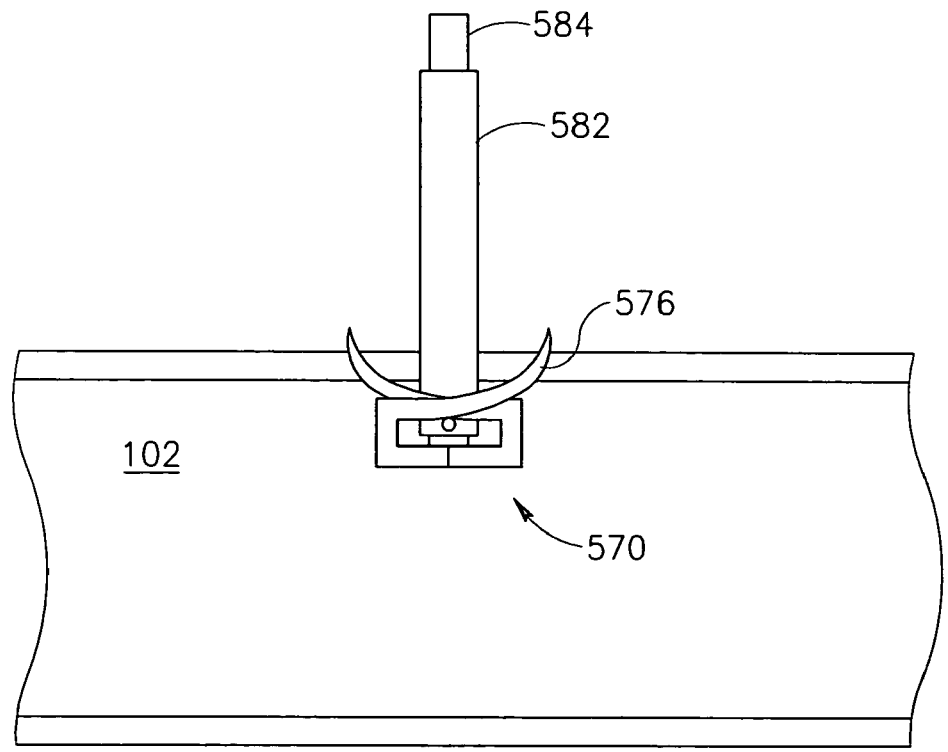

In FIG. 15D, system 580 is retracted, causing spikes 576 to transfix the walls of vessel 102.

Figure 15E:
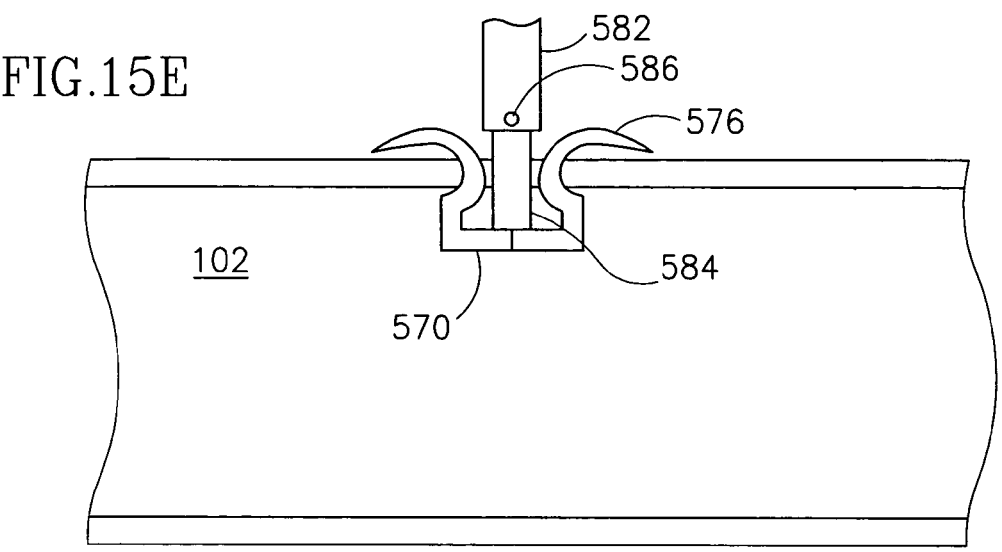

In FIG. 15E, outer tube 590 is retracted, causing pegs 586 to retract and bend spikes 576.

Figure 15F:
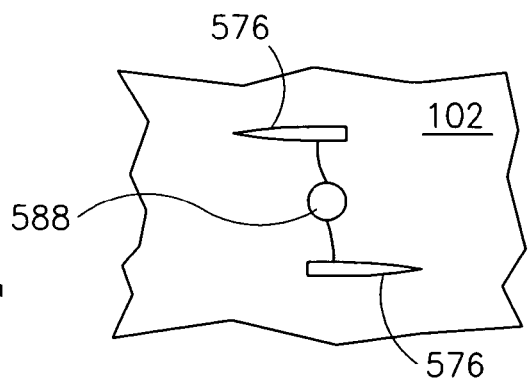

FIG. 15F is a top view showing the relative placement of spikes 576 and tip 588. Also, the distortion of the incision to be sealed is shown.

Figure 15G:
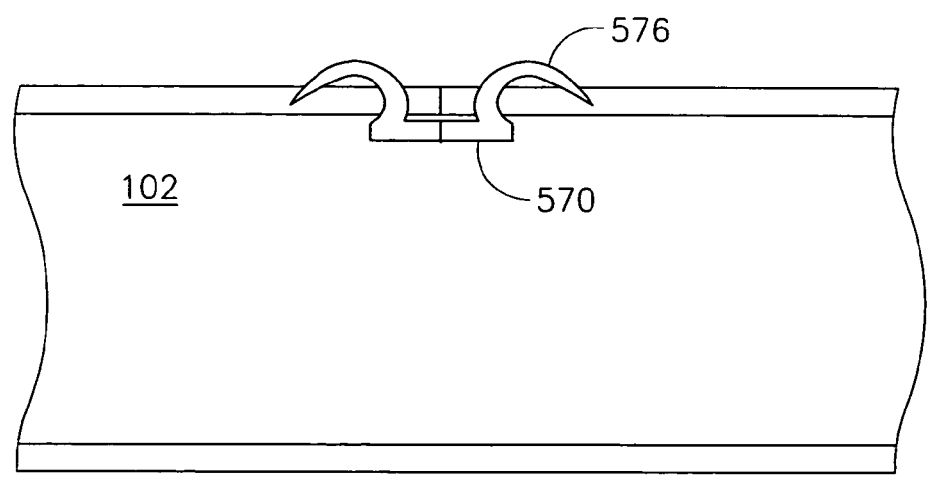

FIG. 15G shows a completely deployed hole closure device 570. In some cases, the movement of pegs 586 is sufficient to completely advance the spikes as shown. Alternatively, the spikes are pushed down using outer tube 590 or pusher 592. Alternatively, retracting rod 584 causes the spikes to bend into the vascular tissue.

FIGS. 16A–16E illustrate additional embodiments of hole closure devices, in accordance with preferred embodiments of the invention.

Figure 16A:
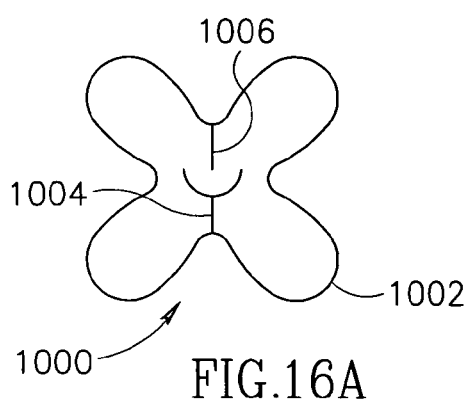
FIGS. 16A–16E illustrate additional embodiments of hole closure devices, in accordance with preferred embodiments of the invention.

FIG. 16A illustrates a device 100, formed of an undulating ring 1002 having two opposing spikes 1004 and 1006. At least one of the spikes has a forked tip. Preferably, device 1000 is planar. Alternatively or additionally, device 1000 is super-elastic. During deployment, device 1000 may be expanded along an axis aligned with the spikes and/or the spikes may be bent in to engage the tissue.

Figure 16B:
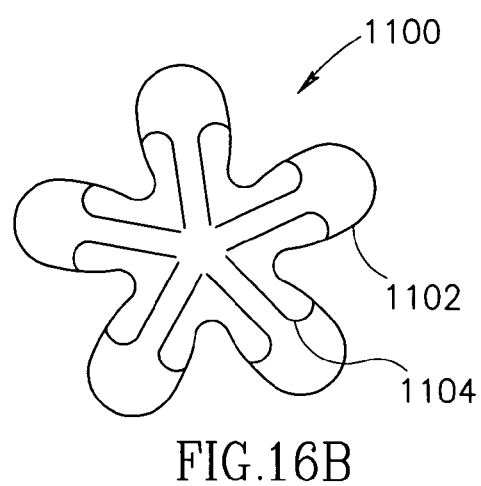

FIG. 16B illustrates a device 1100, which can be without tabs (as shown) or may include tabs (like device 500). A particular feature of this device is that a plurality of spikes 1104 which extend from an undulating ring 1102 do not extent from extreme points of the circumference of ring 1102. As a result, longer spikes can be provided, even when cutting the device from a sheet of metal.

Figure 16C:
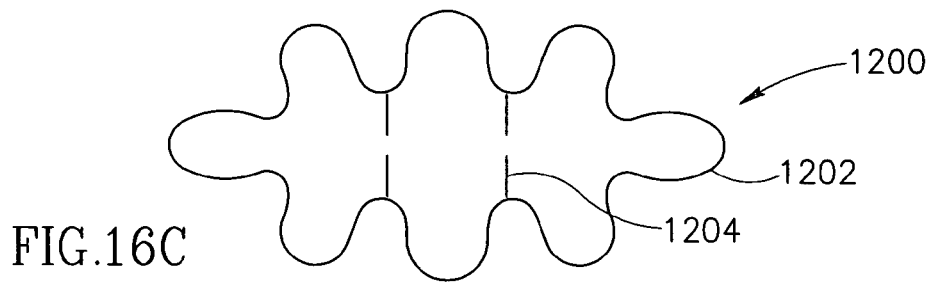

FIG. 16C illustrates a device 1200 similar to device 1000, except that all of a plurality of spike 1204 shown extending from an undulating ellipse 1202 are straight (in this particular embodiment). However, due to the form of ellipse 1202, device 1200 may be more suitable for linear incision and/or for repairing damage caused by accidents.

Figure 16D:
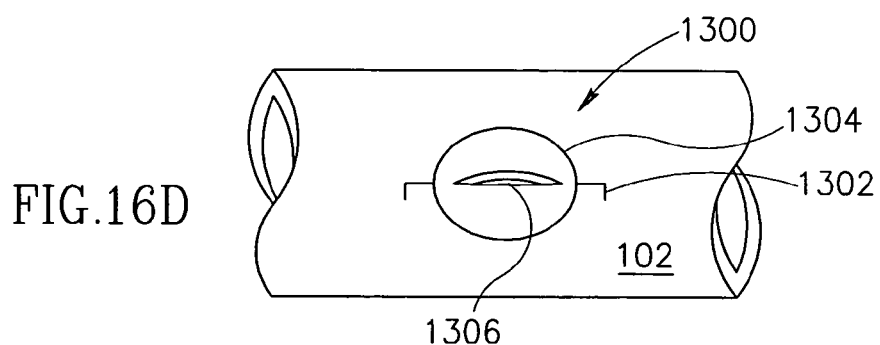
Figure 16E:
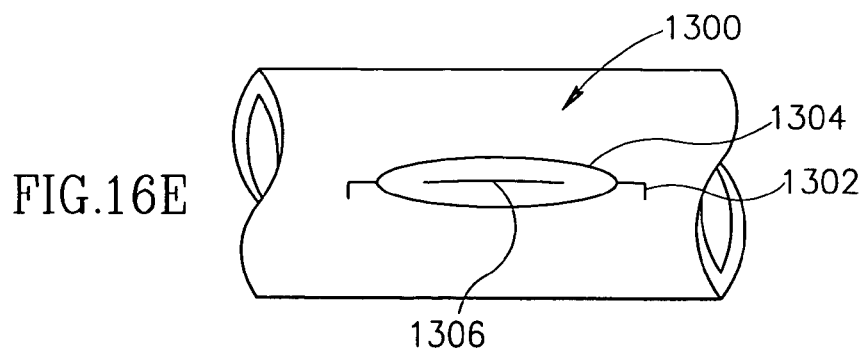

FIGS. 16D and 16E illustrate a tension-based hole closure device 1300, which closes an incision 1306 in a vessel 102 by stretching the vessel so that the incision closes, rather than by directly bringing the lips of the incision together.

In FIG. 16D, incision 1306 is still open and device 1300, comprising a ring 1304 having at least one spike 1302 at either end is inserted into vessel 102. The resting configuration of ring 1304 is as an ellipse if ring 1304 is formed of an elastic, super-elastic or shape-memory material. Alternatively ring 1304 is plastically distorted to an ellipse.

FIG. 16E shows the result. Ring 1304 is now an ellipse, the two spikes 1302 are distanced apart and, by doing so, they stretch vessel 102 radially causing it to close incision 1306.

It should be appreciated that vascular port devices, if used solely as hole closure devices may be made simpler, for example by omitting unnecessary seals and/or by using non-solid members.

It should be appreciated that many of the structures described herein may also be applied to other invasive and/or implantable devices, beyond those used for anastomosis of vascular or non-vascular lumens, especially such devices which are inflatable, expandable and/or otherwise deployed. However, as will be appreciated, that some of the above described structures solve particular problems of port sealing, for example functioning as a port and sealing a hole in a blood vessel.

It will be appreciated that the above described methods of applying a vascular port and sealing a hole may be varied in many ways, including, changing the order of steps and the methods of distortion used. In addition, a multiplicity of various features, both of method and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. Also within the scope of the invention are surgical kits which include sets of medical devices suitable for making a single or a small number of ports or sealing holes of various sizes. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

What is claimed is:

1. A device for sealing a hole in a blood vessel, comprising:
 a ring;
 a plurality of spikes extending from said ring, towards a center of said ring and to a first direction along an axis of said ring, said spikes being adapted for engaging a blood vessel; and
 a plurality of tabs extending substantially radially from said ring,
 wherein rotating said tabs around said ring distorts said ring such that said spikes are rotated in a same direction as said tabs and push together blood vessel lips of a hole in a blood vessel mounted on said spikes, to close a hole in said blood vessel.

2. A device according to claim 1, wherein said device is comprised of a super-elastic material.

3. A device according to claim 1, wherein said spikes are curved.

4. A device according to claim 1, wherein said tabs and said spikes are attached in pairs of one spike and one tab at a plurality of locations along the circumference of said ring, such that the device includes a same number of tabs as spikes.

5. A device according to claim 1, wherein said tabs and said spikes are not attached at same locations along the circumference of said ring.

6. A device according to claim 1, wherein said spikes are evenly arranged around the circumference of said ring.

7. A device according to claim 1, wherein said ring has a resting state in a shape of a circle.

8. A device according to claim 1, wherein said ring has a resting state in a shape of an ellipse with a large ratio between the length of its two axes.

9. A device according to claim 8, wherein said spikes are arranged on opposing sides of said ellipse.

10. A device according to claim 1, wherein said spikes are substantially perpendicular to a plane defined by said ring.

11. A device according to claim 1, wherein said spikes are slanted in a same direction relative to a plane defined by said ring.

12. A device according to claim 1, wherein said ring is radially expandable.

13. A device according to claim 1, wherein said plurality of spikes comprises two spikes.

14. A device according to claim 1, wherein said plurality of spikes comprises three spikes.

15. A device according to claim 1, wherein said plurality of spikes comprises five spikes.

16. A device according to claim 1, wherein said plurality of spikes comprises no more than six spikes.

17. A device according to claim 1, wherein the ring comprises a closed ring located substantially entirely in a single plane.

18. A device according to claim 1, wherein the outer perimeter of the ring is substantially entirely convex.

19. A device according to claim 1, wherein said spikes are substantially perpendicular to a plane defined by said ring, at their meeting point with the ring.

20. A device according to claim 1, wherein the ring is adapted to allow rotation of the tabs.

21. A device according to claim 1, wherein the device is sized and shaped such that rotation of the tabs closes a hole in a blood vessel mounted on the spikes.

22. A cannula having mounted thereon a hole closure device for sealing a hole in a blood vessel, the hole closure device comprising:
a ring;
a plurality of spikes extending from said ring, towards a center of said ring and to a first direction along an axis of said ring, said spikes being adapted for engaging a blood vessel; and
a plurality of tabs extending substantially radially from said ring,
wherein rotating said tabs around said ring distorts said ring such that said spikes are rotated in a same direction as said tabs and push together blood vessel lips of a hole in a blood vessel mounted on said spikes, to close a hole in said blood vessel.

23. A cannula according to claim 22, wherein said cannula comprises an aortic cannula.

24. A cannula according to claim 22, wherein said cannula comprises a femoral cannula.

25. A vascular port having mounted thereon a hole closure device for sealing a hole in a blood vessel, the hole closure device comprising:
a ring;
a plurality of spikes extending from said ring, towards a center of said ring and to a first direction along an axis of said ring, said spikes being adapted for engaging a blood vessel; and
a plurality of tabs extending substantially radially from said ring,
wherein rotating said tabs around said ring distorts said ring such that said spikes are rotated in a same diction as said tabs and push together blood vessel lips of a hole in a blood vessel mounted on said spikes, to close a hole in said blood vessel.

26. A device for sealing a hole, comprising:
an undulating ring having a plurality of inwards pointing portions and a plurality of outwards pointing portions; and
a plurality of spikes, wherein said spikes extend towards a center of said ring from portions of said ring intermediate said inwards and said outwards pointing portions.

27. A device according to claim 26, wherein said device is formed of a single piece of sheet metal, without heat treatment after forming.

28. A device according to claim 26, wherein said device is super-elastic.

29. A method for sealing a hole in a blood vessel, comprising
providing a device including:
a ring;
a plurality of spikes extending from said ring, towards a center of said ring and to a first direction along an axis of said ring, said spikes being adapted for engaging a blood vessel; and
a plurality of tabs extending substantially radially from said ring;
mounting lips of a hole in a blood vessel on the spikes; and
rotating the tabs around the ring, so as to distort said ring such that said spikes are rotated in a same direction as said tabs and the tabs push together the blood vessel lips and close the hole in said blood vessel.

30. A method according to claim 29, wherein rotating the tabs comprises releasing a hold of the tabs and allowing the tabs to move due to elasticity of the device.

* * * * *